US009101742B2

(12) United States Patent
Spera et al.

(10) Patent No.: US 9,101,742 B2
(45) Date of Patent: Aug. 11, 2015

(54) GASTROINTESTINAL APPLICATOR AND METHOD OF USING SAME

(75) Inventors: Gianluca Spera, Rome (IT); Scott R. Ariagno, Lemont, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 2016 days.

(21) Appl. No.: 11/553,546

(22) Filed: Oct. 27, 2006

(65) Prior Publication Data

US 2007/0106213 A1    May 10, 2007

Related U.S. Application Data

(60) Provisional application No. 60/731,350, filed on Oct. 28, 2005.

(51) Int. Cl.
*A61M 31/00* (2006.01)

(52) U.S. Cl.
CPC ..................... *A61M 31/00* (2013.01)

(58) Field of Classification Search
CPC ............ A61M 25/1002; A61M 25/10; A61M 2025/1052; A61M 2025/1086; A61M 2025/1081; A61M 2025/0681; A61M 2025/0004; A61M 25/1011
USPC ............. 604/103.05, 101.03, 102.01, 102.02, 604/102.03; 606/213
See application file for complete search history.

(56) References Cited

U.S. PATENT DOCUMENTS

| 4,368,739 A | * | 1/1983 | Nelson, Jr. ............. 604/516 |
| 4,697,584 A | | 10/1987 | Haynes | |
| 4,798,592 A | * | 1/1989 | Parks ....................... 604/500 |
| 4,832,688 A | | 5/1989 | Sagae et al. | |
| 5,078,701 A | * | 1/1992 | Grassi et al. .............. 604/264 |
| 5,104,377 A | | 4/1992 | Levine | |
| 5,112,310 A | * | 5/1992 | Grobe ...................... 604/175 |
| 5,129,882 A | | 7/1992 | Weldon et al. | |
| 5,171,299 A | | 12/1992 | Heitzmann et al. | |
| 5,221,259 A | | 6/1993 | Weldon et al. | |

(Continued)

FOREIGN PATENT DOCUMENTS

| EP | 0835673 A2 | 4/1998 |
| EP | 1351739 B1 | 5/2006 |

(Continued)

OTHER PUBLICATIONS

PCT Search Report, Mar. 12, 2007, Baxter International.

(Continued)

*Primary Examiner* — Nicholas Lucchesi
*Assistant Examiner* — Weng Lee
(74) *Attorney, Agent, or Firm* — K&L Gates LLP

(57) ABSTRACT

A method and apparatus for dispensing a relatively viscous composition to a wound site at a location within a mammalian body requiring a relatively long and thin catheter for access includes filling a distal tip of the catheter with the composition, directing the distal tip to the wound site, dispensing the composition onto the wound site and then inflating a balloon against the applied composition to enable same to congeal enough so that the composition remains fixed to the wound site after the catheter is removed from the body. In an embodiment the balloon is secured to the catheter such that when air is applied through the catheter to the balloon, the balloon expands longitudinally and distally past a distal end of the catheter.

24 Claims, 19 Drawing Sheets

(56) References Cited

U.S. PATENT DOCUMENTS

| | | | |
|---|---|---|---|
| 5,254,089 A | 10/1993 | Wang | |
| 5,330,446 A * | 7/1994 | Weldon et al. | 604/271 |
| 5,336,178 A | 8/1994 | Kaplan et al. | |
| 5,388,588 A | 2/1995 | Nabai et al. | |
| 5,419,765 A | 5/1995 | Weldon et al. | |
| 5,421,826 A | 6/1995 | Crocker et al. | |
| 5,479,936 A | 1/1996 | Nabai et al. | |
| 5,483,972 A | 1/1996 | Nabai et al. | |
| 5,499,995 A | 3/1996 | Teirstein | |
| 5,571,181 A | 11/1996 | Li | |
| 5,643,315 A | 7/1997 | Daneshvar | |
| 5,649,959 A | 7/1997 | Hannam et al. | |
| 5,669,881 A * | 9/1997 | Dunshee | 604/164.1 |
| 5,704,934 A | 1/1998 | Neuwirth et al. | |
| 5,779,673 A | 7/1998 | Roth et al. | |
| 5,865,816 A * | 2/1999 | Quinn | 604/523 |
| 5,951,583 A | 9/1999 | Jensen et al. | |
| 6,063,061 A | 5/2000 | Wallace et al. | |
| 6,077,261 A | 6/2000 | Behl et al. | |
| 6,090,096 A * | 7/2000 | St. Goar et al. | 604/509 |
| 6,096,021 A | 8/2000 | Helm et al. | |
| 6,146,358 A | 11/2000 | Rowe | |
| 6,217,554 B1 | 4/2001 | Green | |
| 6,290,672 B1 | 9/2001 | Abae | |
| 6,379,373 B1 | 4/2002 | Sawhney et al. | |
| 6,398,780 B1 | 6/2002 | Farley et al. | |
| 6,447,799 B1 | 9/2002 | Ullman | |
| 6,482,179 B1 | 11/2002 | Chu et al. | |
| 6,575,932 B1 | 6/2003 | O'Brien et al. | |
| 6,623,452 B2 | 9/2003 | Chien et al. | |
| 6,729,334 B1 | 5/2004 | Baran | |
| 2001/0001316 A1 | 5/2001 | Nowakowski | |
| 2002/0077656 A1 | 6/2002 | Ginn et al. | |
| 2002/0095114 A1 | 7/2002 | Palasis | |
| 2002/0147462 A1 | 10/2002 | Mair et al. | |
| 2002/0156495 A1 | 10/2002 | Brenneman et al. | |
| 2002/0165581 A1 | 11/2002 | Brucker | |
| 2002/0188170 A1 | 12/2002 | Santamore et al. | |
| 2003/0018357 A1 | 1/2003 | Luthra et al. | |
| 2003/0045865 A1 | 3/2003 | Knapp | |
| 2003/0055313 A1 | 3/2003 | Anderson et al. | |
| 2003/0105469 A1 | 6/2003 | Karmon | |
| 2003/0109899 A1 | 6/2003 | Fisher et al. | |
| 2003/0135091 A1 | 7/2003 | Nakazawa et al. | |
| 2003/0135234 A1 | 7/2003 | Fisher et al. | |
| 2003/0139337 A1 | 7/2003 | Fisher et al. | |
| 2003/0139770 A1 | 7/2003 | Fisher et al. | |
| 2003/0139772 A1 | 7/2003 | Fisher et al. | |
| 2003/0139773 A1 | 7/2003 | Fisher et al. | |
| 2003/0202956 A1 | 10/2003 | Clark et al. | |
| 2004/0098021 A1 * | 5/2004 | Laguna | 606/194 |
| 2004/0260239 A1 * | 12/2004 | Kusleika | 604/101.02 |
| 2004/0267308 A1 * | 12/2004 | Bagaoisan et al. | 606/213 |
| 2005/0107738 A1 | 5/2005 | Slater et al. | |
| 2005/0107826 A1 | 5/2005 | Zhu et al. | |
| 2005/0113798 A1 | 5/2005 | Slater et al. | |
| 2005/0131456 A1 | 6/2005 | Hui | |
| 2005/0131459 A1 | 6/2005 | Akerfeldt | |

FOREIGN PATENT DOCUMENTS

| | | |
|---|---|---|
| WO | WO01/19445 A1 | 3/2001 |
| WO | WO02/05887 A2 | 1/2002 |
| WO | WO02/56954 A2 | 1/2002 |
| WO | WO2004/012805 A2 | 2/2004 |

OTHER PUBLICATIONS

Canadian Office Action issued Apr. 9, 2013 in corresponding Canadian Patent Application No. 2,625,983.

European Office Action for European Application No. 06 839 579.7, dated Apr. 10, 2015.

* cited by examiner

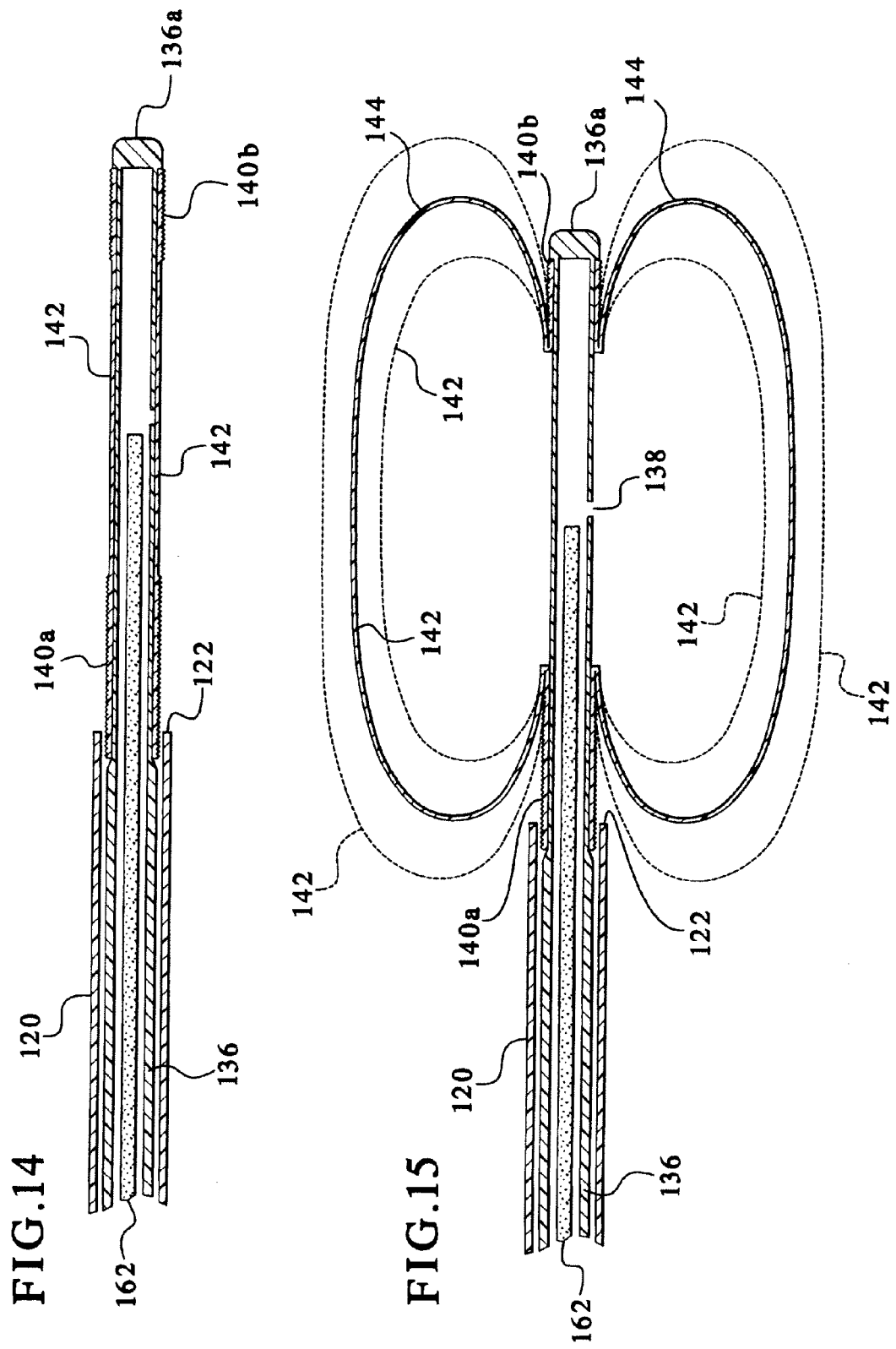

GASTROINTESTINAL APPLICATOR AND METHOD OF USING SAME

PRIORITY CLAIM

This application claims priority to and the benefit as a non-provisional application of provisional U.S. patent application "Gastrointestinal Applicator And Method Of Using Same," Ser. No. 60/731,350, filed Oct. 28, 2005.

BACKGROUND

The present invention relates generally to cross-linked polymeric compositions and to a method of application of such compositions.

U.S. Pat. No. 6,063,061, owned by eventual the assignee of the present invention, the entire contents of which are incorporated herein expressly by reference, describes biocompatible polymeric compositions for application at target sites in a patient's body. The reference describes that one particular use of the compositions is for preventing or inhibiting the formation of tissue adhesions, such as spinal tissue adhesions, following surgery and traumatic injury.

The compositions include a molecular, cross-linked hydrogel, which is configured to enhance its flowability (e.g. the ability to be extruded through a syringe) and its ability to flow onto and conform to sites on or in tissue, including tissue surfaces and defined cavities, e.g. intravertebral spaces, tissue divots, holes, pockets, and the like.

In particular, the gel is taught to flow when the compositions are subjected to stresses above a threshold level, for example when extruded through an orifice or cannula or when packed into a delivery site using a spatula, or the like. The threshold stresses are specified to be in a range from $3 \times 10^4$ Pa to $5 \times 10^5$ Pa. The compositions, however, remain generally immobile when subjected to stresses below the specified levels.

The gels are taught to be packed in a syringe, for example, prior to mechanical disruption. The materials are mechanically disrupted as they are applied through the syringe to the tissue target site. Alternatively, the material is taught to be a cross-linked polymeric material that is stored in a dry form prior to use. The dry material is then loaded into a syringe, for example, hydrated within the syringe, and mechanically disrupted as the material is delivered to the target site.

While the above-described composition has been used effectively in applications that may be reached via a syringe or spatula, e.g., inhibiting tissue adhesions at the spine, the composition is too viscous to be delivered through a long, narrow catheter. Accordingly, the composition has not been used in a typical way for applications requiring such long, narrow catheters, such as wounds, abrasions, cuts or lesions located inside a person's gastrointestinal track.

It is therefore desirable to provide an apparatus and method for supplying the above-described composition, and other target site compositions of similar viscosity, to locations and applications in a mammalian body that require a relatively long and narrow catheter or other passageway for access.

SUMMARY

Described in detail herein are methods and apparatuses for applying therapeutic compositions having viscosities too large to be pushed through an entire length of a relatively long and thin catheter, such as one configured to reach the inside a person's gastrointestinal track. The compositions are of at least one type selected from the group consisting of: (i) a biocompatible polymeric composition; (ii) a molecular, cross-linked hydrogel; (iii) a dry powder; (iv) a partially hydrated gel; and (v) a fully hydrated gel.

The compositions are useful for congealing around wounds internal to a person or animal, for example wounds existing on the inside of the gastrointestinal track. Other uses for the compositions include supplementing tissues, particularly for filling soft and hard tissue regions, including divots, tracts, body cavities, etc., present in muscle, skin, epithelial tissue, connective or supporting tissue, nerve tissue, ophthalmic and other sense organ tissue, vascular and cardiac tissue, gastrointestinal organs and tissue, pleura and other pulmonary tissue, kidney, endocrine glands, male and female reproductive organs, adipose tissue, liver, pancreas, lymph, cartilage, bone, oral tissue, and mucosal tissue. The compositions are further useful for filling soft implantable devices, such as breast implants, in which the material will be protected from degradation by a cellular/enzyme-impermeable barrier or cover. The compositions are additionally useful in other procedures in which it is desirable to fill a confined space with a biocompatible and resorbable polymeric material. Additionally, the compositions may be combined with drugs and other biologically active agents, in which the drugs may be released at the target site over time.

In general, one method for introducing one of the compositions to a location located within a mammalian body is disclosed, wherein a catheter assembly includes an outer tube having a proximal end and a distal end and a balloon catheter located within the outer tube. The method includes: (i) withdrawing the balloon catheter from the proximal end of the outer tube so as to open a space within the outer tube at the distal end of the outer tube; (ii) injecting the composition into the open space created by withdrawing the balloon catheter; (iii) positioning the distal end of the outer tube adjacent to the location (e.g., wound site) within the mammalian body; (iv) inserting the balloon catheter into the proximal end of the outer tube so that a distal end of the balloon catheter pushes the composition out of the distal end of the outer tube and onto the location; and (v) expanding a balloon from the balloon catheter so as to assert pressure to the composition applied to the location.

Pressure is asserted to the composition to accomplish a number of goals. For example the balloon pressure can adjust the composition so that the composition is applied desirously to the location (e.g., to completely and evenly cover a wound or adhesion). Another purpose for using the balloon catheter to assert pressure applied to the body location is to enable the composition to attach or congeal thereto. In one application, the composition forms an artificial scab on the wound. Applying pressure on the composition enables the composition to set-up enough so that the composition will remain at the wound location after the catheter is removed without being washed away by blood or other fluid.

The balloon is expanded from the balloon catheter using air pressure in one embodiment. Here, the doctor may turn a valve so that the balloon catheter is in communication with a positive pressure source, such as a syringe full of air or the hospital's compressed house air.

In one embodiment, withdrawing the balloon catheter from the proximal end of the outer tube is done by manual pulling on the proximal end of the balloon catheter, while holding the outer tube stationary. Likewise, inserting the balloon catheter into the proximal end of the outer tube in one embodiment includes pushing the proximal end of the catheter while holding the tube stationary.

In one embodiment, the doctor withdraws the balloon catheter from the proximal end of the outer tube a distance specified to make the open space within the outer tube have a desired volume. To this end, graduations may be provided at the distal end of the outer tube, which mark known volumetric units, such as millimeters ("ml").

The composition may be stored initially in a syringe. The doctor places the tip of the syringe inside the distal end of the outer tube and injects the composition into the open space vacated by the moved balloon catheter. In one embodiment, the doctor fills the open space at least substantially completely, injecting the composition until it meets the retracted tip of the inner catheter.

The method includes the use of various aids to guide or position the distal end of the outer tube within the person or animal. An introducer may be provided from an entry point into the body (e.g., mouth, anus or abdominal area) into the organ or tissue needing attention. The doctor then slides the outer tube and catheter through and into the organ or other area. The doctor may also use the camera or a flexible endoscope to position the distal end of the outer tube at the injection location. The catheter assembly may also house a guide wire, which provides increased rigidity and positionability. The guide wire may be placed though an inner lumen defined by the catheter or a separate catheter located within the outer tube.

During the procedure, the doctor may move: (i) the catheter back and forth within the outer tube or (ii) the entire catheter assembly back and forth to adjust the composition so as to be applied desirously to the location. During this back and forth movement, the balloon may be inflated at least one time to: (i) adjust the composition so as to be applied desirously to the location; or (ii) hold the composition to the location to enable the composition to be attached thereto.

After the composition has been applied as desired by the doctor, the balloon is deflated for the last time. The catheter assembly is removed from the introducer and the body. The introducer is removed from the body, and an entry perforation, if any, is sewn closed.

To carry out the above-described method, in one embodiment, a medical kit is provided, which includes a source of the above-described composition. The kit also includes a catheter assembly, which includes an outer tube having a proximal end and a distal end and a balloon catheter located within the outer tube. The balloon catheter is moveable within the outer tube so as to create an open space in the outer tube at the distal end thereof.

The source, which can be a syringe filled with the composition for example, contains enough composition to fill the open space. If the source is a syringe, the syringe can be configured for dual use: (i) to supplying the composition to the catheter assembly; and (ii) to thereafter supply air to inflate a balloon of the balloon catheter.

The balloon catheter includes a proximal end and a distal end. The balloon is located at the distal end. The proximal end of the balloon catheter includes a valve used to allow or disallow air to pressurize and expand the balloon. It may also include additional connectors to receive one or more guide wire.

The kit includes other items, such as a tip protector fitted to the distal end of the outer tube. The kit also includes a bag that can be sealed to enclose the composition source and catheter assembly prior to use. The kit may also store an introducer.

Also, to carry out the above-described method, in one embodiment, an improved medical catheter assembly is provided. The assembly includes an outer tube having a proximal end and a distal end and a balloon catheter located within the outer tube. The balloon catheter is moveable within the outer tube so as to create an open space within the outer tube at the distal end thereof. The open space is sized to hold one of the compositions described herein, wherein the composition is applied from a source in an amount sufficient to cover a wound site or other application. A distal end of the outer tube includes a connector configured to sealingly accept the source of the composition. The connector can be a female luer connector. The distal end of the outer tube can also include graduations indicating volumetric units for the open space.

In an embodiment, the catheter assembly includes ergonomic sheath and catheter grips, which aid the doctor in maneuvering the catheter with respect to the stationary sheath. The sheath grips can have a variety of ergonomic features, such as ribbed grips, grasping wells and/or grasping flanges. The catheter grip can be slotted such that when not grasped the catheter grip slides freely over the catheter. But when the doctor compresses the slotted portion of the grip, the grip clamps to the catheter so that the doctor can move the catheter with respect to the sheath. In any case, in an embodiment, the catheter grip and sheath grip provide audible and/or tactile feedback to the doctor when the catheter is in a full extended, e.g., balloon inflating position.

The composition is preloaded into a syringe in one embodiment. An adapter is provided having one end that connects sealingly to the syringe, e.g., via luer lock fittings. The other end of the adapter is sized to accept a distal end of the sheath for loading composition into the sheath. This end also includes a nut that threads onto a portion of the adapter housing an elastomeric washer. A metal cannula is inserted into the adapter. The sheath end fits over the metal cannula and within the cylindrical elastomeric washer.

When the doctor tightens the nut, the nut translates an integral internal collar causing it to compress the washer longitudinally along an axis of the adapter. The longitudinal compression of the washer causes the inner diameter of the washer to compress radially onto the sheath and in turn compress the sheath onto the cannula for a seal-tight exchange of composition from the syringe, through the adapter, to the sheath.

In one embodiment, the balloon portion of the catheter is at least one of a silicone and latex member that is sutured or wire wound at either end a sufficient distance to hold the balloon tight enough against the catheter that the balloon can be expanded outwardly along the central axis of the catheter as well as radially outwardly from the catheter. This allows the catheter to extend distally past the end of the catheter enough such that the balloon protects the patient from being poked by the relatively rigid catheter end. The balloon provides a relatively bluntly, rounded end surface for contact. This configuration also increases the ability of the doctor to use the distal end of the balloon for composition application if desired, e.g., to provide more pressure and/or more localized pressure.

To the above described ends, in one embodiment a method for introducing a composition to a location located within a mammalian body via a catheter assembly including an outer tube having a proximal end and a distal end and a catheter located within the outer tube is provided. The method includes: (i) withdrawing the catheter from the proximal end of the outer tube so as to open a space within the outer tube at the distal end of the outer tube; (ii) injecting the composition into the open space; (iii) positioning the distal end of the outer tube adjacent to the location within the mammalian body; and (iv) inserting the catheter into the proximal end of the outer tube so that a distal end of the catheter pushes the composition out of the distal end of the outer tube and onto the location.

In one embodiment, the catheter is a balloon catheter, and which includes the further step of expanding a balloon from the balloon catheter so as to assert pressure to the composition applied to the location.

In one embodiment, asserting pressure to the composition accomplishes at least one of: (i) adjusting the composition so as to be applied desirously to the location; (ii) holding the composition to the location to enable the composition to be attached thereto; and (iii) using a distal end of the balloon to apply pressure.

In one embodiment, expanding the balloon from the balloon catheter includes at least one of: (i) opening a valve located at the proximal end of the balloon catheter; (ii) allowing pressurized air to communicate fluidly with the balloon; (iii) pressing a syringe filled with air, the syringe in fluid communication with the balloon; and (iv) inflating the balloon distally and longitudinally past and end of the catheter.

In one embodiment, at least one of: (i) withdrawing the catheter from the proximal end of the outer tube includes pulling on a proximal end of the catheter with respect to the tube; and (ii) inserting the catheter into the proximal end of the outer tube includes pushing the proximal end of the catheter with respect to the tube.

In one embodiment, withdrawing the catheter from the proximal end of the outer tube includes withdrawing the catheter a distance specified to make the open space have a desired volume.

In one embodiment, injecting the composition onto the open space includes at least one of: (i) transferring the composition from a syringe to the open space; (ii) injecting the composition such that it at least substantially fills the open space; and (iii) sealing an end of the outer tube between an elastomeric member and a metal cannula.

In one embodiment, positioning the distal end of the outer tube within the mammalian body includes at least one of: (i) sliding the tube through an introducer, the introducer providing access to the location within the body; and (ii) using a camera to position the distal end of the outer tube.

In one embodiment, the method includes using a guide wire for rigidity, the guide wire inserted into one of: (i) an inner lumen defined by the catheter and (ii) an additional guide wire inlet provided by the catheter.

In one embodiment, the catheter includes a balloon, and which includes at least one additional step selected from the group consisting of: (i) inflating the balloon multiple times to accomplish one or more objective; (ii) inflating the balloon distally past and end of the catheter; (iii) deflating the balloon after the composition has congealed to the location; and (iv) withdrawing the outer tube and balloon catheter from the body after deflating the balloon.

In one embodiment, the method includes moving the catheter back and forth within the outer tube to adjust the composition so as to be applied desirously to the location.

In one embodiment, the catheter includes a balloon, and which includes inflating the balloon at least one time during the time when the balloon is moved back and forth to accomplish at least one of: (i) adjusting the composition so as to be applied desirously to the location; and (ii) holding the composition to the location to enable the composition to be attached thereto.

In one embodiment, the method includes inserting the catheter into the mammalian body via an entry point selected from the group consisting of: (i) the mouth; (ii) the anus; (iii) the abdomen; and (iv) the ribcage.

It is therefore an advantage of the present disclosure to provide a method for supplying relatively high viscosity compositions described and incorporated herein to locations and applications in a mammalian body that require a relatively long and narrow catheter or other passageway.

It is another advantage of the present disclosure to provide a kit for performing the method.

It is a further advantage of the present disclosure to provide a catheter assembly for performing the method.

It is still a further advantage of the present disclosure to provide a catheter assembly which is easily and skillfully maneuverable.

It is yet another advantage of the present disclosure to provide a catheter assembly with a ready sealable composition transfer apparatus.

Moreover, it is an advantage of the present disclosure to provide a balloon portion of the catheter that reduces patient discomfort, increases pressure application and localization flexibility.

Additional features and advantages are described herein, and will be apparent from, the following Detailed Description and the figures.

BRIEF DESCRIPTION OF THE FIGURES

FIG. 14 is a sectioned elevation view of an embodiment of a distal end of the catheter, guide wire and sheath, wherein the catheter is in an expandable position and balloon portion is deflated.

FIG. 15 is a sectioned elevation view of an embodiment of a distal end of the catheter, guide wire and sheath, wherein the catheter is in an expandable position and balloon portion is inflated.

DETAILED DESCRIPTION

Figure 1A:
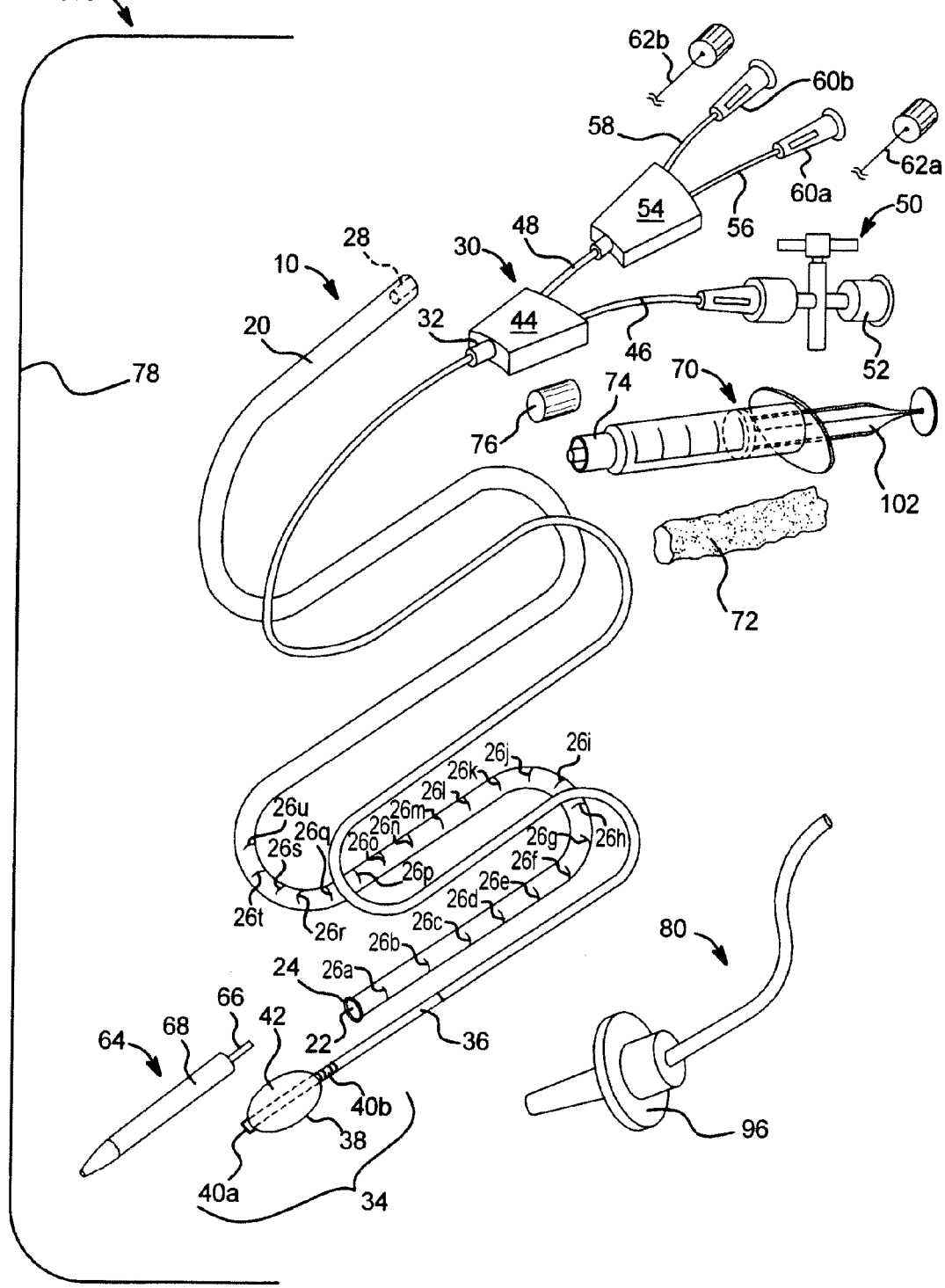
FIGS. 1A and 1B are exploded perspective views of different embodiments of a kit including a catheter assembly, a source of composition, and other items.

Referring now to the drawings and in particular to FIG. 1A, one embodiment of a kit housing the apparatus configured to perform the method described herein is illustrated by kit 100. Kit 100 includes a catheter assembly 10. Catheter assembly 10 is shown pulled apart into its main components, namely, an outer tube 20 and balloon catheter 30. Balloon catheter 30 is normally inserted into a lumen 22 defined by outer tube 20.

Outer tube 20 may be constructed of any suitable biocompatible material, such as polyolefin, polyester or other polymeric materials. Outer tube 20 may have any suitable dimension, such as being 200 to 2000 millimeters ("mm") in length, 20 to 200 mm outside diameter and 10 to 170 mm, inner diameter. Outer tube 20 in an embodiment is transparent, translucent or otherwise see-through, so that balloon catheter 30 may be viewed while disposed within outer tube 20.

Outer tube 20 includes or defines a female luer 24 at its distal end. Female luer 24 is configured to mate at least substantially sealingly with a source of the composition 72, such as syringe 70, which is filled as packaged with composition 72. In the illustrated embodiment, connector 24 is a female luer. Alternatively, connector 24 is a male type luer connector or a different type of medical fluid connector. In a preferred embodiment, the outer diameter of connector 24 is as small as possible, so that connector 24 does not inhibit the insertion of outer tube 20 into a person or animal.

Graduations 26a to 26u are placed or marked on the distal end of outer tube 20. Graduations 26 (referring collectively to graduations 26a to 26u) mark a known volumetric quantity defined by lumen 22. For example, graduations 26 can meter a volume of one milliliter ("ml") of composition 72. Graduations 26 can indicate any suitable volumetric units and are not limited to indicating milliliters. Moreover, any suitable number of graduations 26 may be provided. The purpose of graduations 26 is discussed in detail below.

A thickened portion 28 is provided at the proximal end of outer tube 20. Thickened portion 28 is sized and configured to engage a collar 32 of balloon catheter 30 frictionally and removably. As indicated by FIG. 1A, when balloon catheter 30 is inserted fully into outer tube 20, such that thickened portion 28 is slid over and engaged with collar 32, a distal section 34 of balloon catheter 30 extends past the distal end of outer tube 20 (which is highlighted by connector 24).

Balloon catheter 30 includes a long narrow tube 36, which can be constructed of any suitable biocompatible material, such as polyolefin, polyester or other polymeric materials. Tube 36 may have any suitable dimensions, such as being 200 to 2000 mm in length, 5 to 160 mm outside diameter and 1 to 150 mm, inner diameter. In one embodiment, balloon catheter 30 has a relatively or very stiff pre-incorporated or pre-inserted guide wire that allows for a smooth flow of the high viscosity gel.

Narrow tube 36 is covered by a tightly fitting sheath 38. Sheath 38 is made of any suitable material, such as polyolefin. Sheath 38 enables air to be supplied through a thin annular passage defined by the outer diameter of tube 36 and the inner diameter of sheath 38 to a balloon portion 42. Windings 40a and 40b are provided on the either side of balloon portion 42, located at the distal section 34 of tube 36 of balloon catheter 30, in such a manner to create the pressurization needed to expand balloon portion 42 when a positive pressure is applied to the above-described annular passage.

The proximal end of tube 36 mates or is integral with collar 32, which in an embodiment is integral with housing 44. Housing 44 is in turn in fluid communication with a pair of input tubes 46 and 48. Input tube 46 extends to a valve 50. Valve 50 enables the doctor to either enable or not enable pressurized air to flow through valve 50, through tube 46, through housing 44, through the annular passage between tube 36 and sheath 38 to expand balloon portion 42 of balloon catheter 30. Valve 50 includes an inlet connector 52, which in an embodiment is a female luer of the same size and thread pitch as female luer 24 located at the end of outer tube 20. Such configuration enables the same syringe 70 to be used: (i) to load the distal end of outer tube 20 with a desired composition 72 (described below) and then (ii) to pressurize balloon portion 42 of balloon catheter 30 when needed.

Inlet tube 48 extends from housing 44 to a second housing 54. Second housing 54 is in turn in fluid communication with a second pair of inlet tubes 56 and 58. Inlet tubes 56 and 58 in turn each communicate with a female luer 60a and 60b, respectively. Female luers 60a and 60b in an embodiment accept guide wires 62a and 62b, respectively. Guide wires 62a and 62b provide a desired rigidity to balloon catheter 30 and thus to catheter assembly 10. It should be appreciated that narrow tube 36 of balloon catheter 30 defines a lumen (not seen), through which a guide wire 62a or 62b may be inserted.

Catheter assembly 10 as packaged is provided with a tip protector 64. Tip protector 64 includes a thin male extension 66 which fits into the lumen of tube 36, at the distal end of the tube. An outer portion 68 of tip protector 64 is sized and configured to mate with outer tube 20 of catheter assembly 10. In an embodiment, outer portion 68 of tip protector 64 is a male lure configured to thread onto female luer 24 of outer tube 20.

Kit 100 includes additional items. For example, kit 100 is provided with a syringe 70, which has been discussed previously herein. Syringe 70 as packaged is filled with a desired composition 72. Desired composition 72 is provided in an amount suitable to perform the target operation or application. Various suitable compositions are described in U.S. Pat. No. 6,063,061, the entire contents of which have been incorporated herein previously.

One embodiment for composition 72 includes a polymer. The polymer is capable of being cross-linked and of being hydrated to form a hydrogel. Exemplary polymers include proteins selected from gelatin, collagen (e.g. soluble collagen), albumin, hemoglobin, fibrinogen, fibrin, fibronectin, elastin, keratin, laminin, and derivatives and combinations thereof. Alternatively, the polymer may comprise a polysaccharide, such as a glycosaminoglycan, a starch derivative, a cellulose derivative, a hemicellulose derivative, xylan, agarose, alginate, chitosan, and combinations thereof. As a further alternative, the polymer may comprise a non-biologic hydrogel-forming polymer, such as polyacrylates, polymethacrylates, polyacrylamides, polyvinyl polymers, polylactide-glycolides, polycaprolactones, polyoxyethylenes, and derivatives and combinations thereof. Other features of the polymer and other forms of composition 72 are described in the incorporated patent. Composition 72 is packed into syringe 70 as a gel in one preferred embodiment. The viscosity of the gel is well-suited for the method of application discussed below.

Syringe 70 is provided with a male luer 74, which in one embodiment is configured to mate with female luers 24 and 52 of outer tube 20 and valve 50, respectively, and as described previously. A female luer cap 76 is inserted as packaged onto male luer 74 of syringe 70 to seal the composition 72 within syringe 70. Syringe 70 is then packaged within a closeable and sealable bag or container 78 along with assembly 10.

Bag or container 78 is additionally sized to hold an introducer 80. Introducer 80 in one embodiment is an endoscope or scope, which may otherwise be termed a gastro-scope or colon-scope, etc. The gastro-scope introduces the catheter assembly 10 into the human or animal body through the mouth, as seen for example in FIG. 2A. This may be done for upper gastrointestinal bleeding or legions. A colon-scope type introducer on the other hand enables access through the anus of the patient, as discussed for example in connection with FIG. 2B. A further type of access is shown in FIG. 2C, in which access is made through the abdomen or rib area of the patient. Any of the above types of access is suitable for use with the method and apparatus of the examples described herein. In an embodiment, introducer 80 having a cuff 96 is sized and configured for any of the different types of access. Alternatively, kit 100 includes a particular type of introducer 80, which is selected for a particular type of access.

Figure 1B:
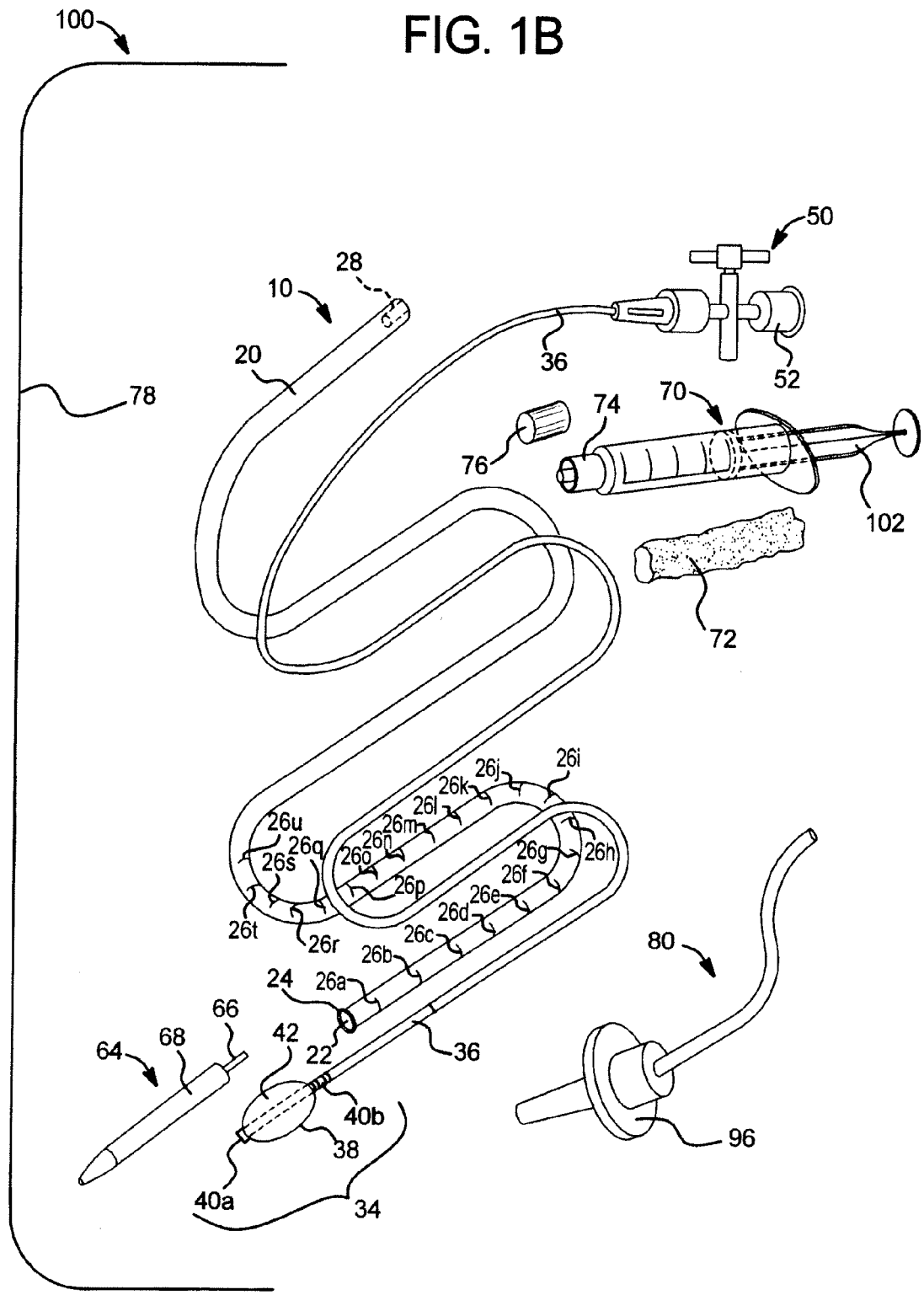

Referring now to FIG. 1B, one preferred embodiment for kit 100 and catheter assembly 10 is illustrated. Here, a relatively or very stiff guide wire (not illustrated) is pre-incorporated or pre-inserted into narrow tube 36 via a separate passageway or lumen (not illustrated) within tube 36. The pre-incorporated or pre-inserted guide wire allows for a smooth flow of the viscous fluid through narrow tube 36, enhances directional ability and enhances pressure applying ability. The pre-incorporated or pre-inserted guide wire can be removably threaded into the passageway or lumen within tube 36, so that the guide wire can be removed if it is not needed or desired. The pre-incorporated or pre-inserted guide wire enables certain ones of the proximal end tubes to be eliminated. For example, one or more or all of inlet tubes 48, 56 and 58 may be eliminated, which could also eliminate the need for second housing 54. In the illustrated embodiment, second housing 54 and inlet tubes 48, 56 and 58 are eliminated and tube 36 is extended to valve 50. First housing 44 can still be provided for one of the guide wires 62a and 62b.

Figure 2A:
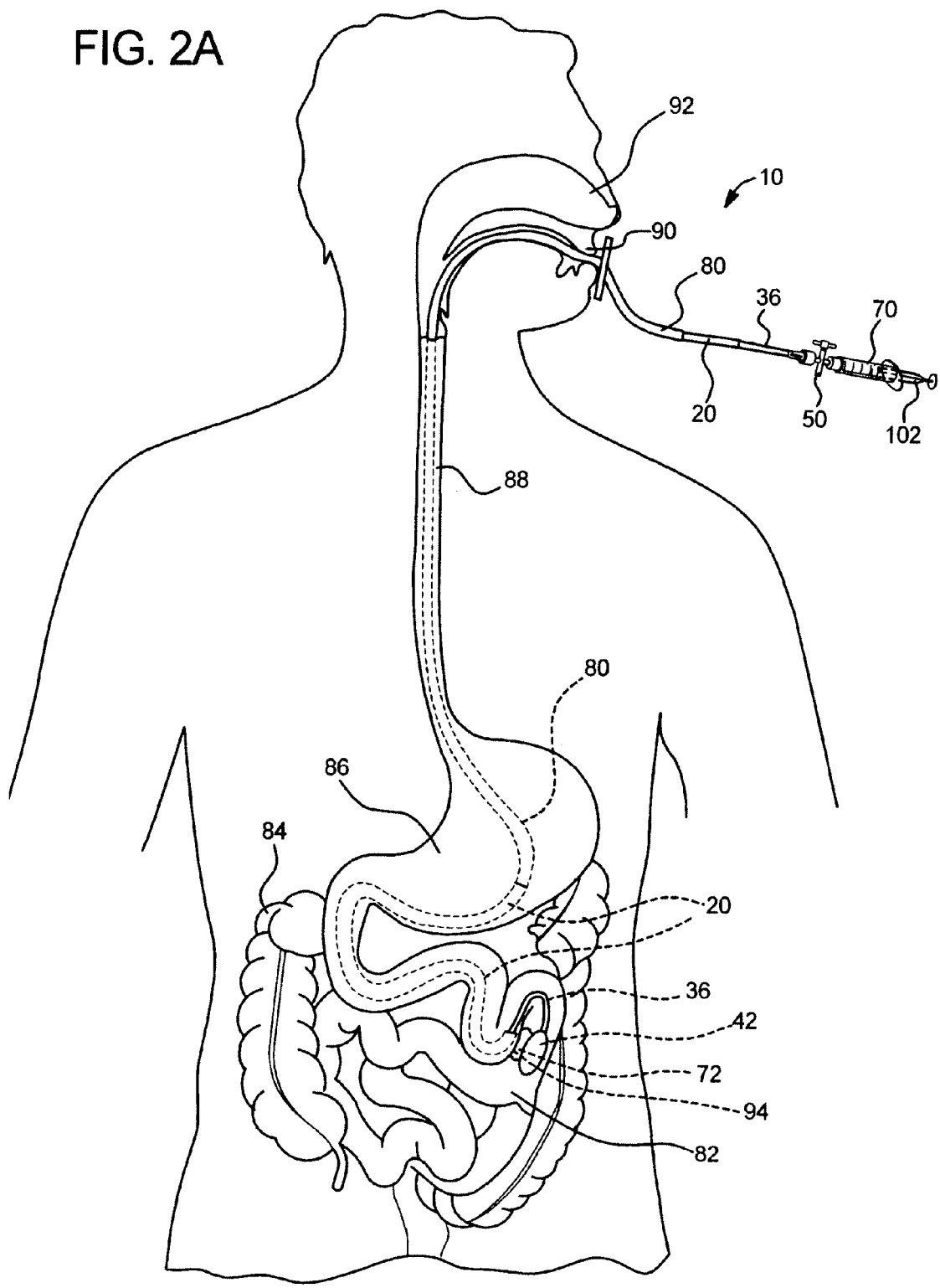
FIGS. 2A to 2C are cutaway perspective views showing a person's gastrointestinal track and the application of the method and apparatus described herein from different access points.
Figure 2B:
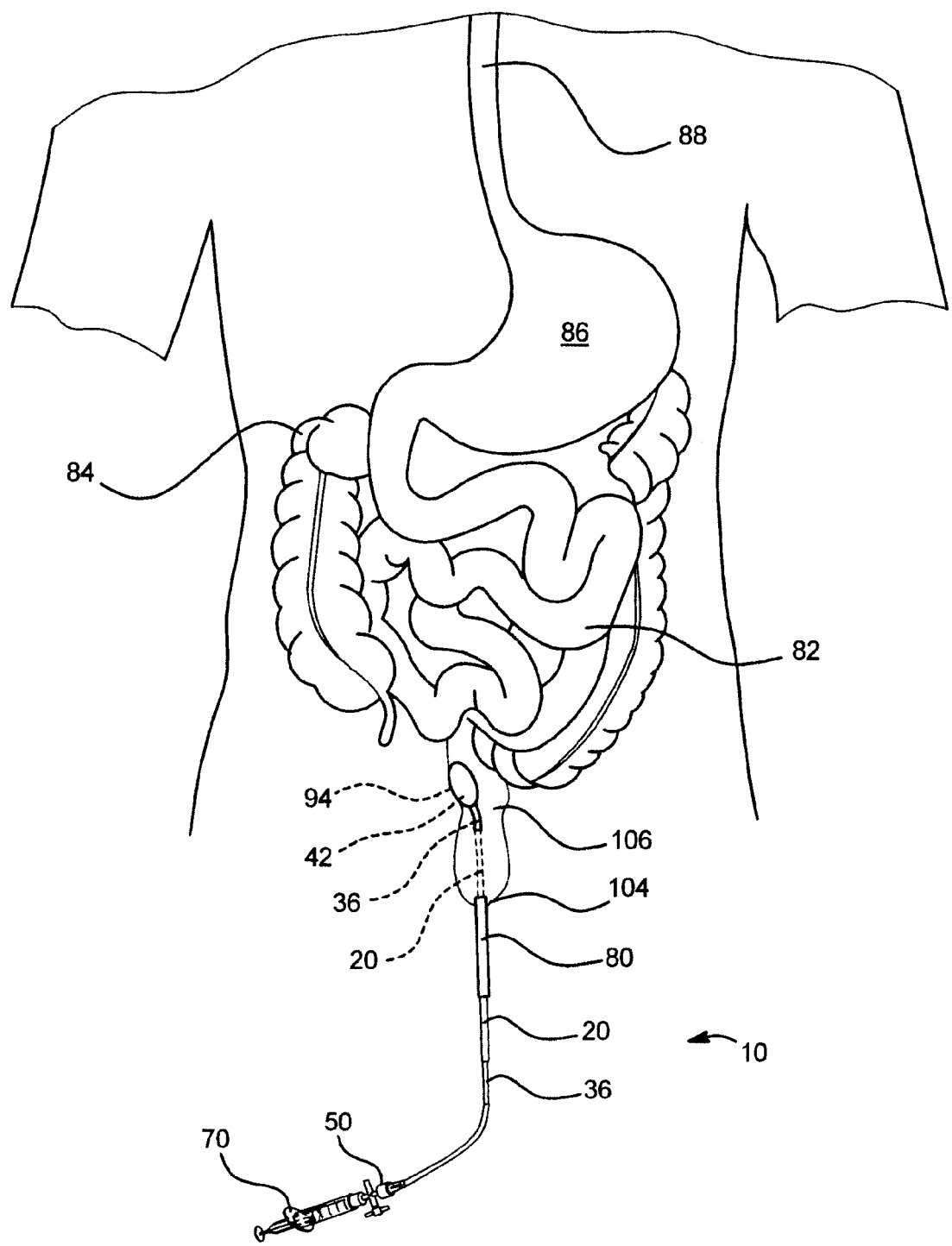
Figure 2C:
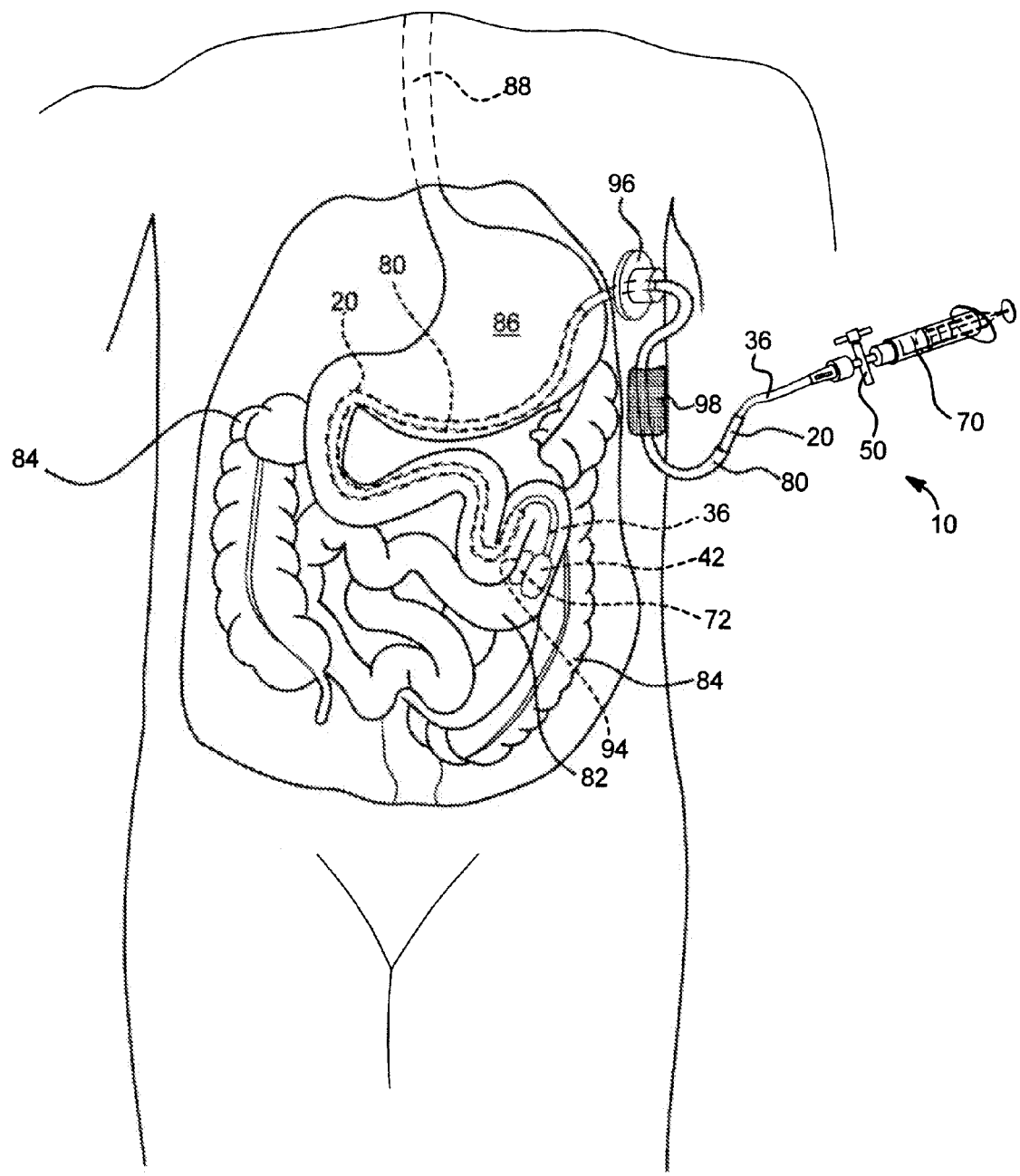

Referring now to FIGS. 2A to 2C, one application for the catheter assembly 10 and other components described above in connection with kit 100 is illustrated. Here, catheter assembly 10 is used to dispense composition 72 at a wound site or legion 94 residing at an inner wall of the patient's small intestine 82. For reference, the patient's large intestine 84, stomach 86 and esophagus 88 are also illustrated in FIGS. 2A to 2C. FIG. 2A further illustrates that the esophagus 88 is in biological communication with the patient's mouth 90 and nose 92.

In FIG. 2A, introducer 80 is of a gastro-scope type, which introduces catheter assembly 10 into the patient's body through the patient's mouth 90. In the illustrated embodiment, introducer 80 extends into the patient's stomach 86. Introducer 80 therefore guides assembly 10 into the patient's stomach 86. Thereafter, the doctor maneuvers assembly 10 into the patient's small intestine 82 and to wound site 94. In an alternative embodiment, introducer 80 is extended further into the patient's small intestine 82. Further alternatively, introducer 80 extends only into the patient's esophagus 88 as desired by the doctor.

Catheter assembly 10 is used to dispense composition 72 at wound site 94 according to the method described in connection with FIGS. 3 to 11. As illustrated in FIGS. 2A to 2C and explained in more detail below, balloon portion 42 of tube 36 of balloon catheter 30 is expanded and shown holding composition 72 against wound site 94. As described in detail below, this is done to enable composition 72 to congeal to wound site 94 before catheter assembly 10 is removed. In the illustrated embodiment, composition 72 is used to form a temporary scab at wound site 94. As such, it is necessary to ensure that composition 72 has set-up or congealed enough so that once the catheter assembly 10 is removed, the composition 72 will not be washed away by blood or other fluids or materials.

As described in U.S. Pat. No. 6,063,061, composition 72 is configured to biodegrade or be absorbed into the body after a period of time after which wound site 94 has healed. As seen in FIG. 2A, balloon portion 42 of balloon catheter 30 in an embodiment is inflated via compressed air from syringe 70, through valve 50, housing 44 (optionally), through the annular lumen between tube 36 and tightly fitting sheath 38 to balloon portion 42. A guide wire 62a or 62b may be inserted through female luers 60a and 60b, housing 54, housing 44 and through the lumen of tube 36 as needed to direct tube 36 of balloon catheter 30 to wound site 94.

FIG. 2B shows an alternative access location through the patient's anus. Here, introducer 80 is inserted through the patient's anus 104. Introducer 80 may thereafter extend as far into the patient's anal cavity or colon as desired by the doctor. As before, catheter assembly 10 and syringe 70 are used to deposit composition 72 at wound site 94 and thereafter inflate balloon portion 42 of thin tube 36 of balloon catheter 30 to hold composition 72 in place until it has congealed properly. In the illustrated embodiment, wound site 94 is located within the patient's colon 106, making insertion through the patient's anus advantageous.

FIG. 2C shows a further alternative access location through the patient's abdominal or ribcage area. Here, introducer 80 is punctured through the patient's skin and wall of stomach 86. Introducer 80 may thereafter extend as far into the patient's stomach and/or small intestine 82 as desired by the doctor. As mentioned above, introducer 80 includes a cuff 96, which may be secured to the patient. Additionally, tape 98 may be employed to help hold introducer 80 fixed with respect to the patient. As before, catheter assembly 10 and syringe 70 are used to deposit composition 72 at wound site 94 and thereafter inflate balloon portion 42 of thin tube 36 of balloon catheter 30 to hold composition 72 in place until it has congealed properly.

Referring now to FIGS. 3 to 11, one embodiment for dispensing composition 72 properly at wound site 94 shown in connection with FIGS. 2A and 2C is illustrated. It should be appreciated that the method described herein may be used to apply composition 72 at any desired point along the patient's gastrointestinal tract, such as at an inner wall of stomach 86, anywhere within small intestine 82 or anywhere within large intestine 84. Furthermore, composition 72 may also be deposited within esophagus 88, anal area, or within any of the other organs, tissues and/or locations described herein.

Figure 3:
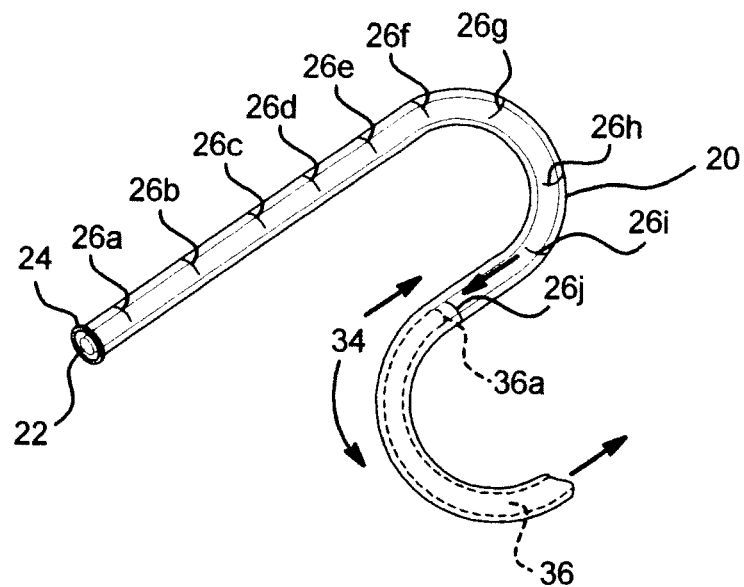
FIG. 3 is a perspective view of a distal end of the catheter showing a first step of one example of the composition application method.

FIG. 3 shows the distal end of outer tube 20. The distal tip of outer tube 20 as described in connection with FIG. 1A is highlighted by female luer 24 or any other suitable connector. The distal end of outer tube 20 is also provided with graduations 26, here ten graduations 26a to 26j. Those graduations correspond with graduations 26a to 26j shown on syringe 70 in FIG. 4.

In a first filling step of FIG. 3, the doctor holds the proximal end of outer tube 20 fixed and pulls balloon catheter 30, e.g., by grasping housing 44, backward and out of the proximal end of outer tube 20. The doctor pulls balloon catheter 30 a distance such that the distal tip 36a of tube 36 of balloon catheter 30 is retracted to a desired point within outer tube 20. In the illustrated embodiment, the distal tip of tube 36 is retracted until it reaches graduation 26j, which for example could indicate that lumen 22 defined by outer tube 20 defines a volume of 10 milliliters from the distal end of tube 36 located at graduation 26j to the distal tip of outer tube 20 (highlighted by female luer 24).

Figure 4:
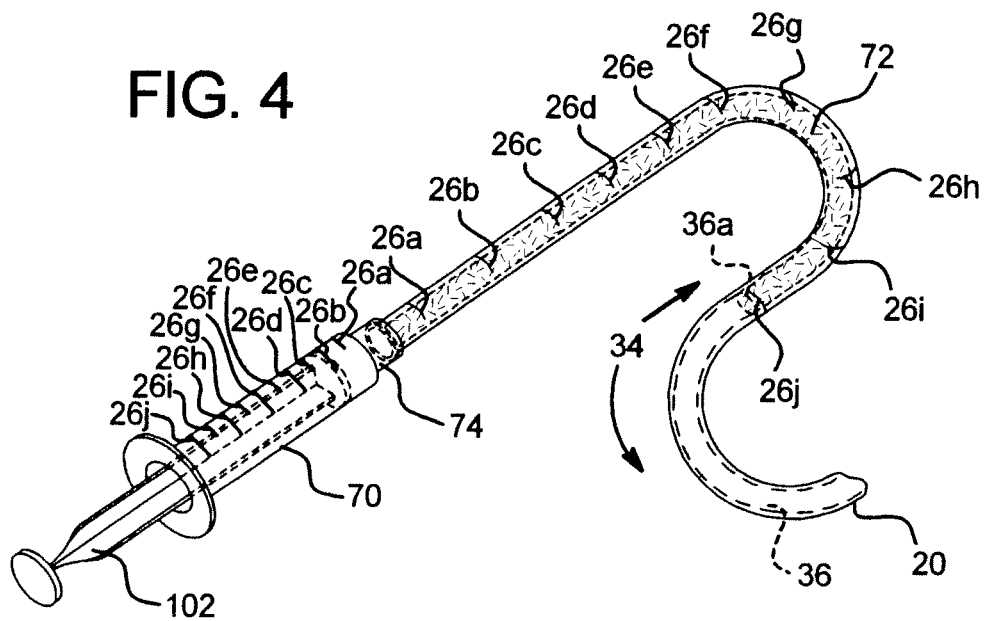
FIG. 4 is a perspective view of the distal end of the catheter connected to a source of the composition showing a second step of one example of the composition application method.

In a second filling step illustrated in FIG. 4, the doctor removes cap 76 (shown in FIGS. 1A and 1B) from male luer connector 74 of syringe 70. The doctor fastens the syringe 70 to the distal tip of outer tube 20 by connecting male luer 74 of syringe 70 to female luer 24 of outer tube 20. Next, the doctor pushes plunger 102 of syringe 70 to dispel composition 72, preloaded into syringe 70, into the open space of lumen 22 of outer tube 20. In an embodiment one to ten milliliters (for example) of composition 72 is pushed into the distal end of outer tube 20. In a further embodiment one to ten millililters of composition 72 is pushed into the distal end of outer tube 20. If smaller syringes are desired, then multiple syringes may be used to provide the desired volume of composition 72. The composition 72 fills lumen 22 to the distal tip 36a of narrow tube 36 of the balloon catheter 30, which resides at graduation 26j of outer tube 20. The viscosity of composition 72 is such that it will not spill out of the end of tube 20 without mechanical actuation or flow between tubes 36 and 20.

Figure 5:
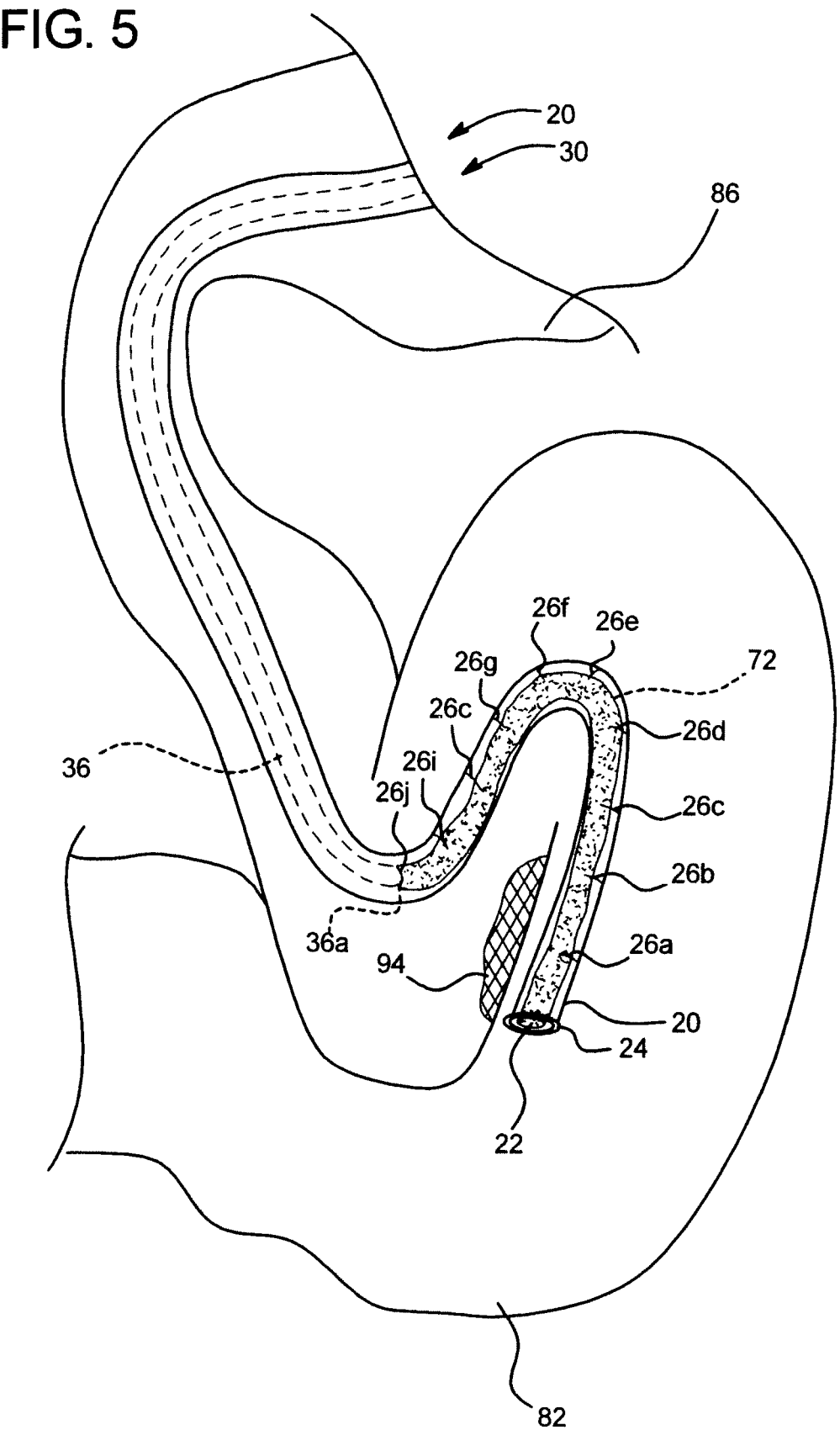
FIG. 5 is an enlarged view of an application area of the person's gastrointestinal track with the distal end of the catheter positioned to illustrate a third step of one example of the medical composition application method.

FIGS. 5 to 11 show a closer view of a portion of small intestine 82 and stomach 86. As seen in FIG. 5, wound site 94 occurs along an inner wall of small intestine 82. In this next step, the doctor via any of the access ways discussed above inserts catheter assembly 10 (with tube 36 of balloon catheter 30 in the retracted position and composition 72 held within outer tube 20) to a location within small intestine 82 that is desirable to dispense composition 72 onto wound site 94. It should be appreciated that any of the steps discussed in connection with FIGS. 5 to 11 can be done in connection with a camera or other type of visual recording/imaging device (not illustrated), so that the doctor can see catheter assembly 10 within the patient's small intestine 82. In the illustrated embodiment, the doctor pushes the distal end of outer tube 20 highlighted by female luer 24 to a lower end of wound site 94. For purposes of illustration, a pair of arrows indicates that tube 20 and balloon catheter 30 are pushed collectively, so that assembly 10 moves down into the small intestine 82.

Figure 6:
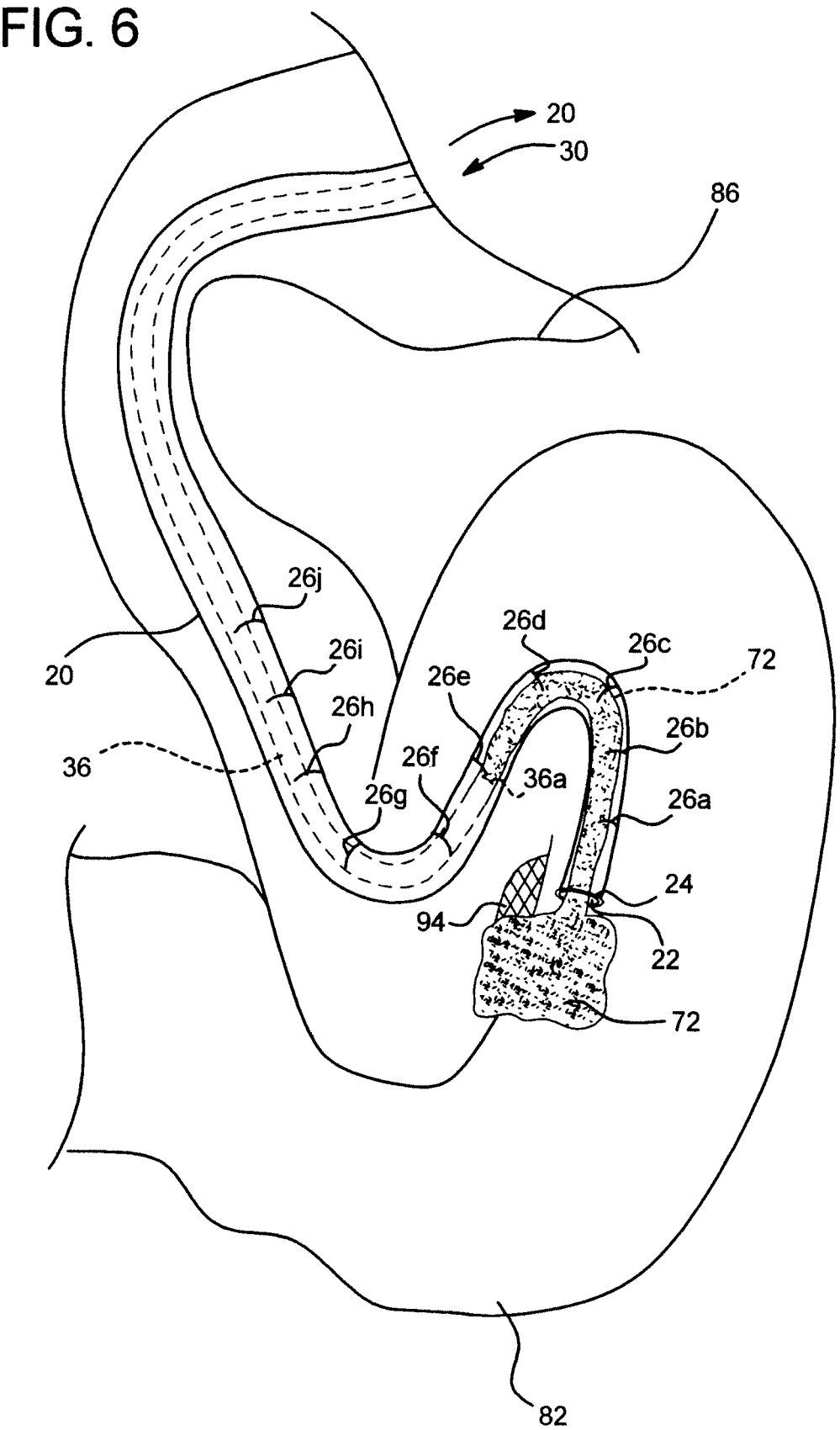
FIG. 6 is an enlarged view of the application area of the person's gastrointestinal track with the balloon catheter and outer tube of the assembly moved relatively to illustrate a fourth step of one example of the medical composition application method.

Referring now to FIG. 6, a further step in the method is illustrated. Here, the doctor begins to retract the overall assembly 10 including outer tube 20, while at the same time inserting balloon catheter 30 into outer tube 20, which creates a relative motion, similar to that of toothpaste being applied to a toothbrush, wherein outer tube 20 moves upward along wound site 94 of small intestine 82, while at the same time tube 36 of balloon catheter 30 moves downward within outer tube 20, expelling composition 72 from tube 20. The relative motion of tube 36 with respect to outer tube 20 causes composition 72 to be dispensed onto wound site 94, as directed by the doctor. In the illustrated embodiment, the doctor has dispensed approximately half of the composition 72 by pushing tube 36 from graduation 26j to graduation 26e. This action can dispense for example, five milliliters of the total 10 milliliters of composition 72 through the distal end of outer tube 20. That five milliliters of composition 72 is dispensed through lumen 22 of outer tube 20 onto wound site 94 as seen in FIG. 6. For purposes of illustration, arrows are shown indicating that tube 20 is being moved upwardly out of the patient, while balloon catheter 30 is being inserted back into outer tube 20.

Figure 7:
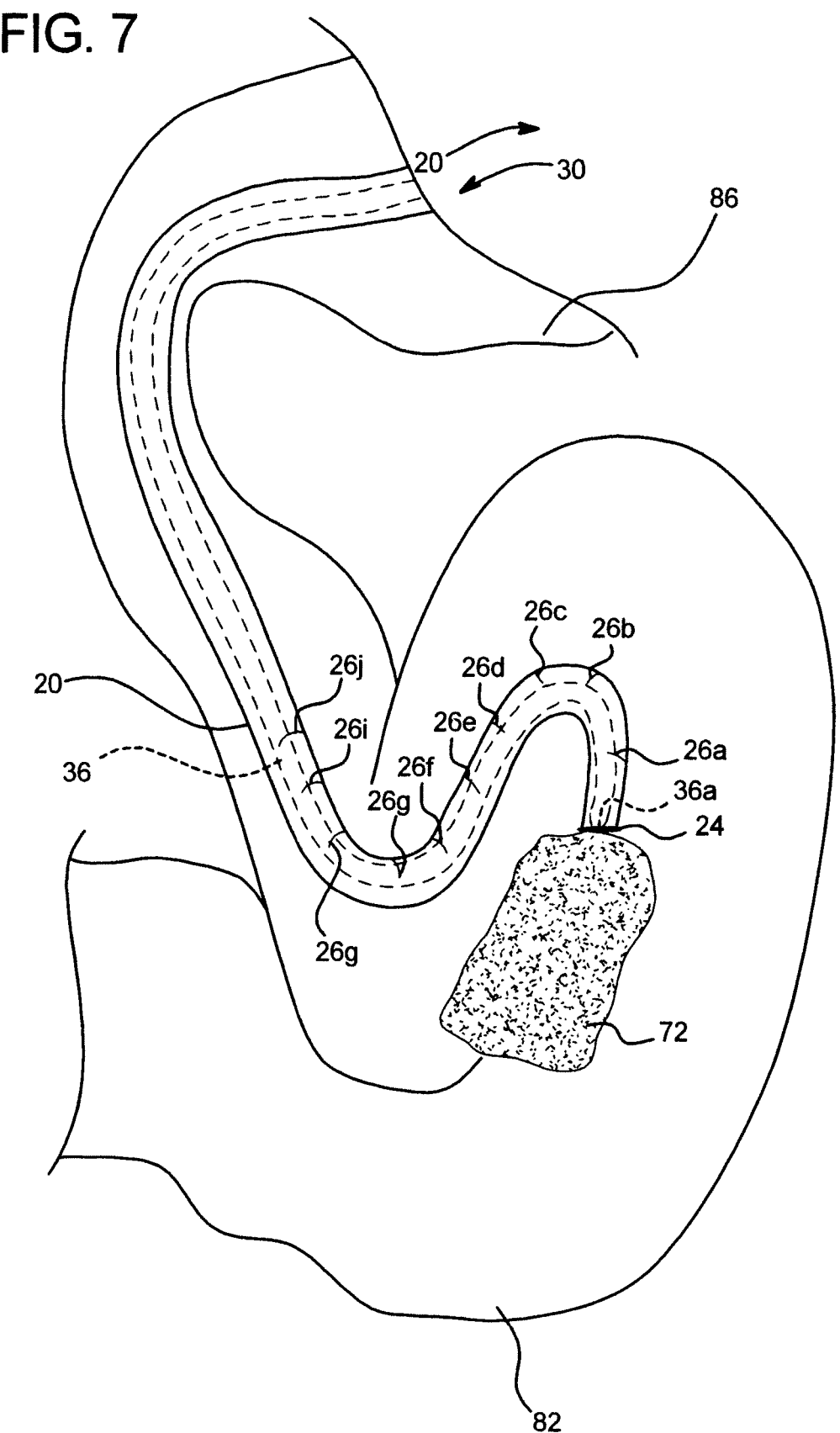
FIG. 7 is an enlarged view of the application area of the person's gastrointestinal track with the balloon catheter and outer tube of the assembly moved relatively to illustrate a fifth step of one example of the medical composition application method.

Referring now to FIG. 7, the doctor continues to dispense composition 72 so that eventually all or substantially all of the composition 72 is dispensed from the distal end of outer tube 20 onto wound site 94, which in FIG. 7 is no longer visible. In the illustrated embodiment, the doctor pulls the overall catheter assembly 10, including outer tube 20, further upward along the small intestine 82 and out of the patient. At the same time, the doctor continues to reinsert balloon catheter 30 into outer tube 20. This action causes thin tube 36 of balloon catheter 30 to travel further towards the distal end of outer tube 20. In FIG. 7, tube 36 travels from graduation 26e to the end of outer tube 20, causing the, e.g., the remaining five milliliters of composition 72 to be dispensed onto the wound site. Accordingly, the doctor has dispensed the full ten milliliters of composition 72 at the desired location within the patient's small intestine 82. For purposes of illustration, the arrows continue to show that outer tube 20 is being pulled out of the patient, while balloon catheter 30 is being reinserted into outer tube 20.

Figure 8:
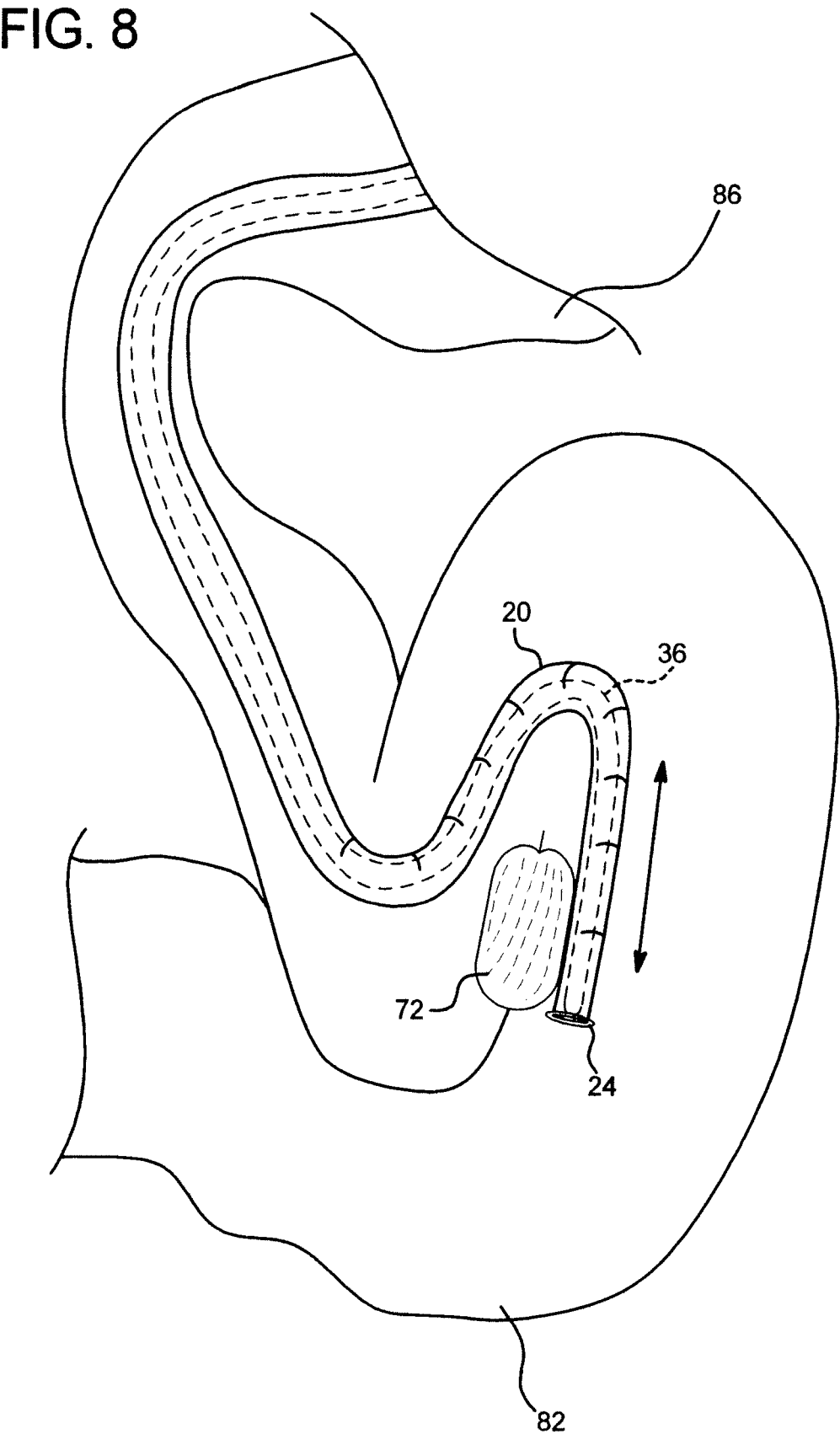
FIG. 8 is an enlarged view of the application area of the person's gastrointestinal track with the balloon catheter and outer tube of the assembly moved together to illustrate a sixth step of one example of the medical composition application method.

Referring now to FIG. 8, another step or portion of the procedure is illustrated. Here, the doctor moves outer tube 20 and inner tube 36 in tandem back and forth along composition 72, which has been applied to the wound site. This back and forth motion may be done to disperse composition 72 so that it covers the wound site more fully and/or evenly. Also, the pressure applied by outer tube 20 helps composition 72 to congeal or stick to the inner wall of small intestine 82. To perform this portion of the procedure, the doctor moves catheter assembly 10 back and forth relative to introducer 80.

Figure 9:
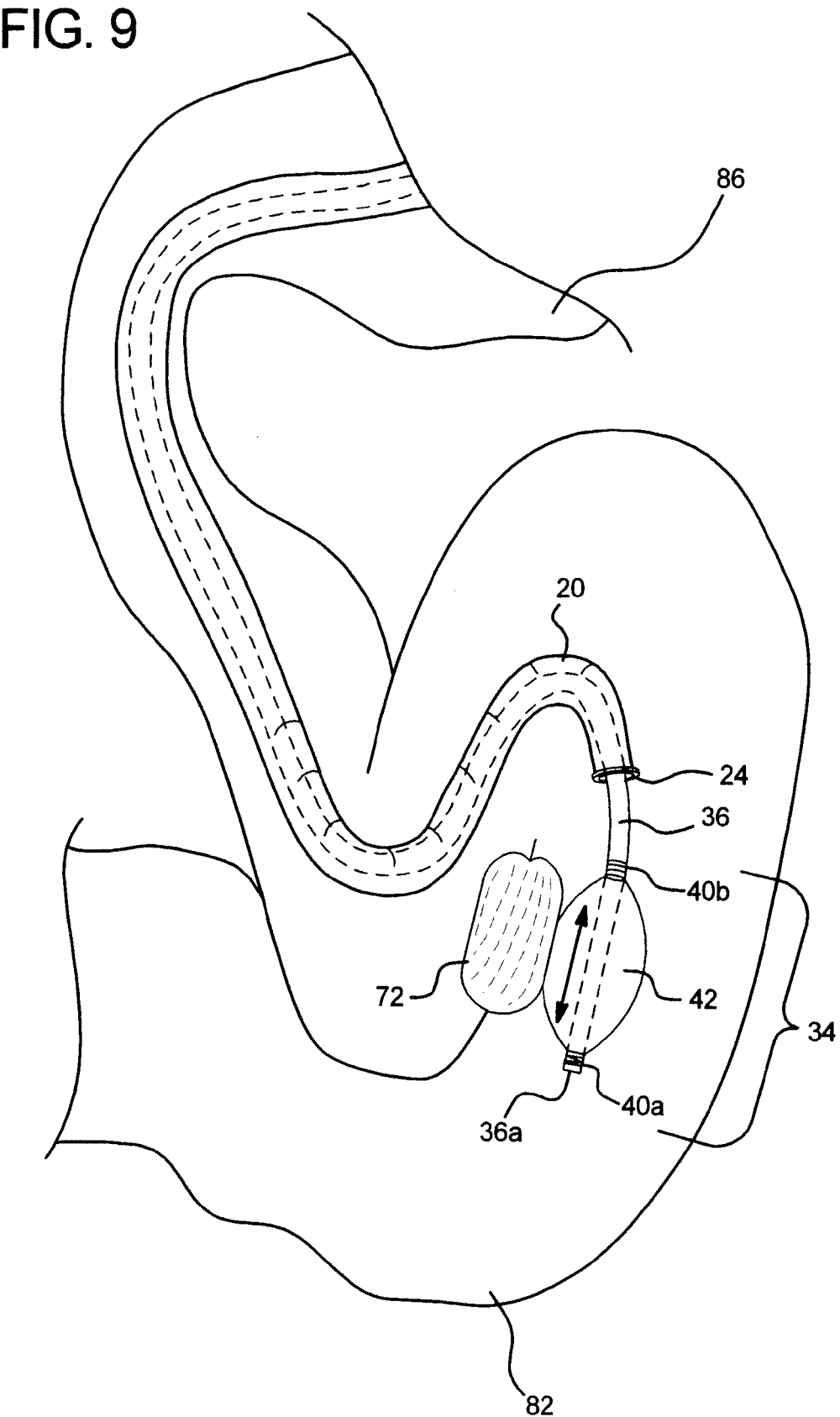
FIG. 9 is an enlarged view of the application area of the person's gastrointestinal track with the balloon catheter and outer tube of the assembly moved relatively to illustrate a seventh step of one example of the medical composition application method, wherein the balloon of the catheter is partially inflated.

Referring now to FIG. 9, a similar procedure as described in FIG. 8 is performed. Here however, balloon portion 42 of balloon catheter 30 is at least partially inflated. To enable balloon portion 42 to inflate, the doctor pushes tube 36 of balloon catheter 30 fully into outer tube 20. As seen in FIGS. 1A and 1B, such relative motion is completed when thickened portion 28 of outer tube 20 is fitted frictionally onto collar 32 of housing 44 of balloon catheter 30. When balloon catheter 30 is inserted fully as described into outer tube 20, distal portion 34 of tube 36 of balloon catheter 30 extends outside of the distal tip of outer tube 20. Balloon portion 42 can thereafter be expanded, for example, by connecting syringe 70 to valve 50 and pressing plunger 102 of syringe 70. It should be appreciated however that any suitable source of positive air pressure, such as a cylinder or house air, may be employed to expand balloon portion 42.

The at least partial expansion of balloon portion 42 can increase the amount of mechanical force applied to composition 72 to further smooth, even and/or desirably disperse composition 72 on the wound site, as desired by the doctor. Accordingly, the arrow shows that the at least partially expanded balloon portion 42 is moved back and forth over composition 72. The doctor accomplishes such procedure by moving either: (i) the catheter assembly 10 with the balloon portion 42 expanded back and forth within fixed introducer 80; or (ii) moving balloon catheter 30 in its expanded state, while holding outer tube 20 fixed.

Figure 10:
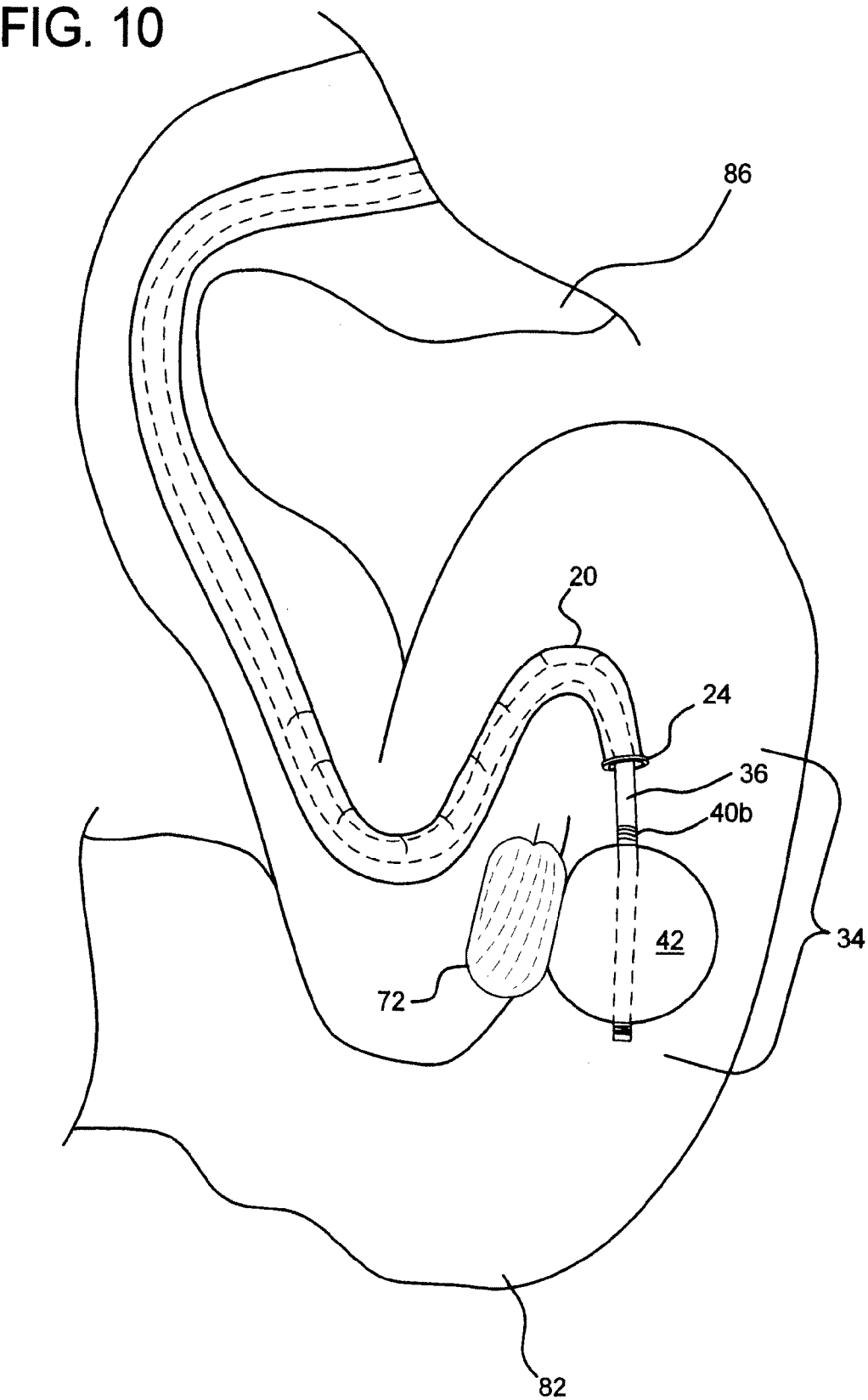
FIG. 10 is an enlarged view of the application area of the person's gastrointestinal track in which the balloon of the catheter is inflated fully to illustrate an eighth step of one example of the medical composition application method.

Referring now to FIG. 10, another step of the method or procedure is illustrated. Here, balloon portion 42 of tube 36 of balloon catheter 30 is inflated fully. The full inflation causes balloon portion 42 to be wedged within small intestine 82 to apply a relatively large amount of mechanical force to composition 72. The primary purpose of applying this relatively large amount of force is to help composition 72 set-up or congeal before catheter assembly 10 is removed from the patient. The inflated balloon portion 42 may be pressed against composition 72 for a period of five seconds to thirty minutes, for example. It should be appreciated that the doctor may also move the fully inflated balloon portion 42 back and forth over composition 72 as shown and described in connection with FIG. 9 to further smooth and disperse composition 72 if necessary.

It is also contemplated to perform the steps shown in connection with FIGS. 8 to 10 multiple times as desired by the doctor until composition 72 is deposited as desired. This method or procedure it should be appreciated provides the doctor with ample flexibility to dispense and disperse composition 72 properly.

Figure 11:
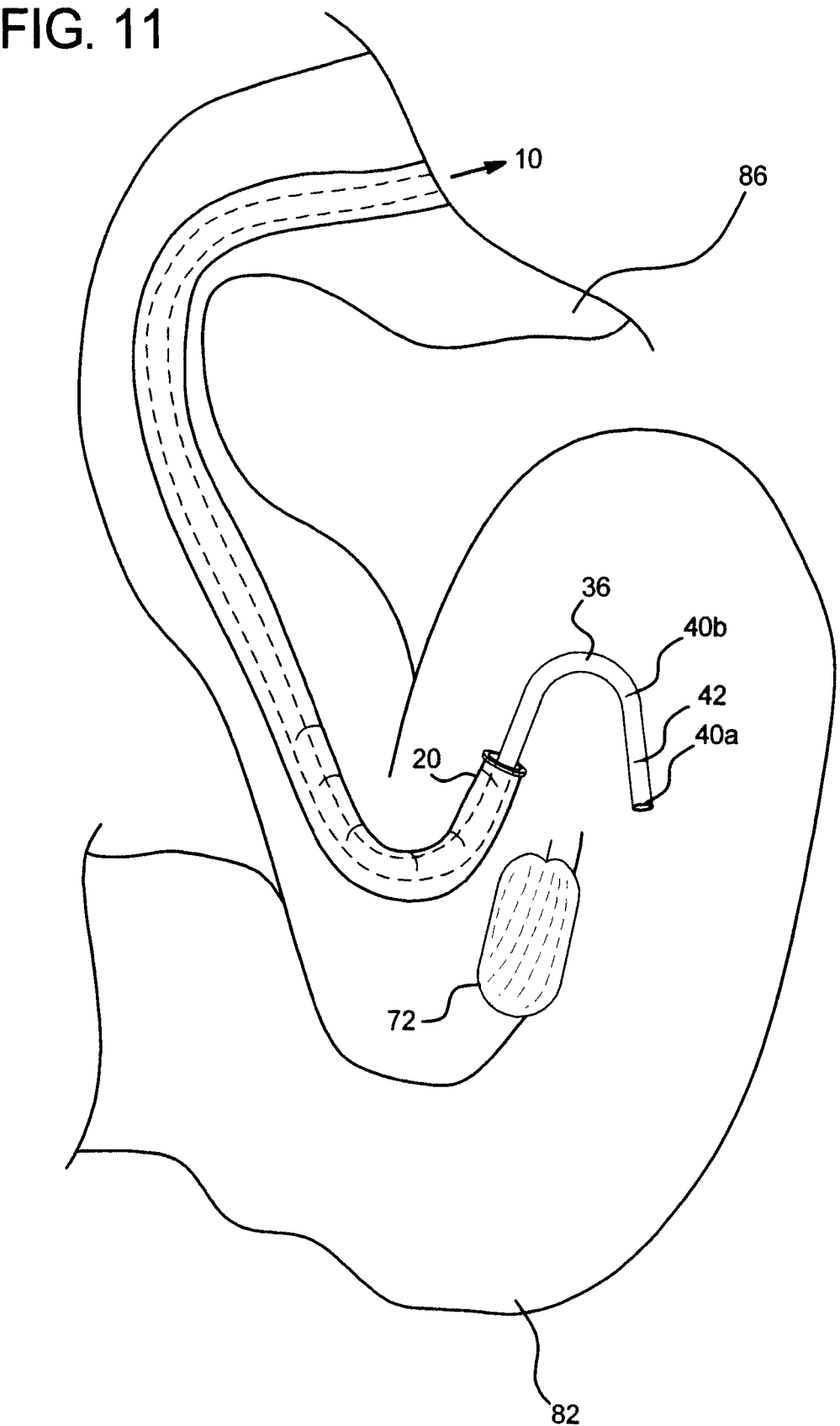
FIG. 11 is an enlarged view of the application area of the person's gastrointestinal track with a deflated balloon catheter and outer tube of the assembly removed together to illustrate a ninth step of one example of the medical composition application method.

Referring now to FIG. 11, when the doctor is assured that composition 72 has been properly congealed onto the wound site, the doctor deflates balloon portion 42 and removes catheter assembly 10 from the small intestine 82 and the patient as illustrated by the arrow in FIG. 11. If desired, the doctor can draw the balloon portion 42 of the balloon catheter 40 into the outer tube 20 prior to removal. The doctor pulls catheter assembly 10 out of the body through introducer 80. Next, the doctor removes introducer 80 from the body and performs any necessary suturing.

Figure 12:
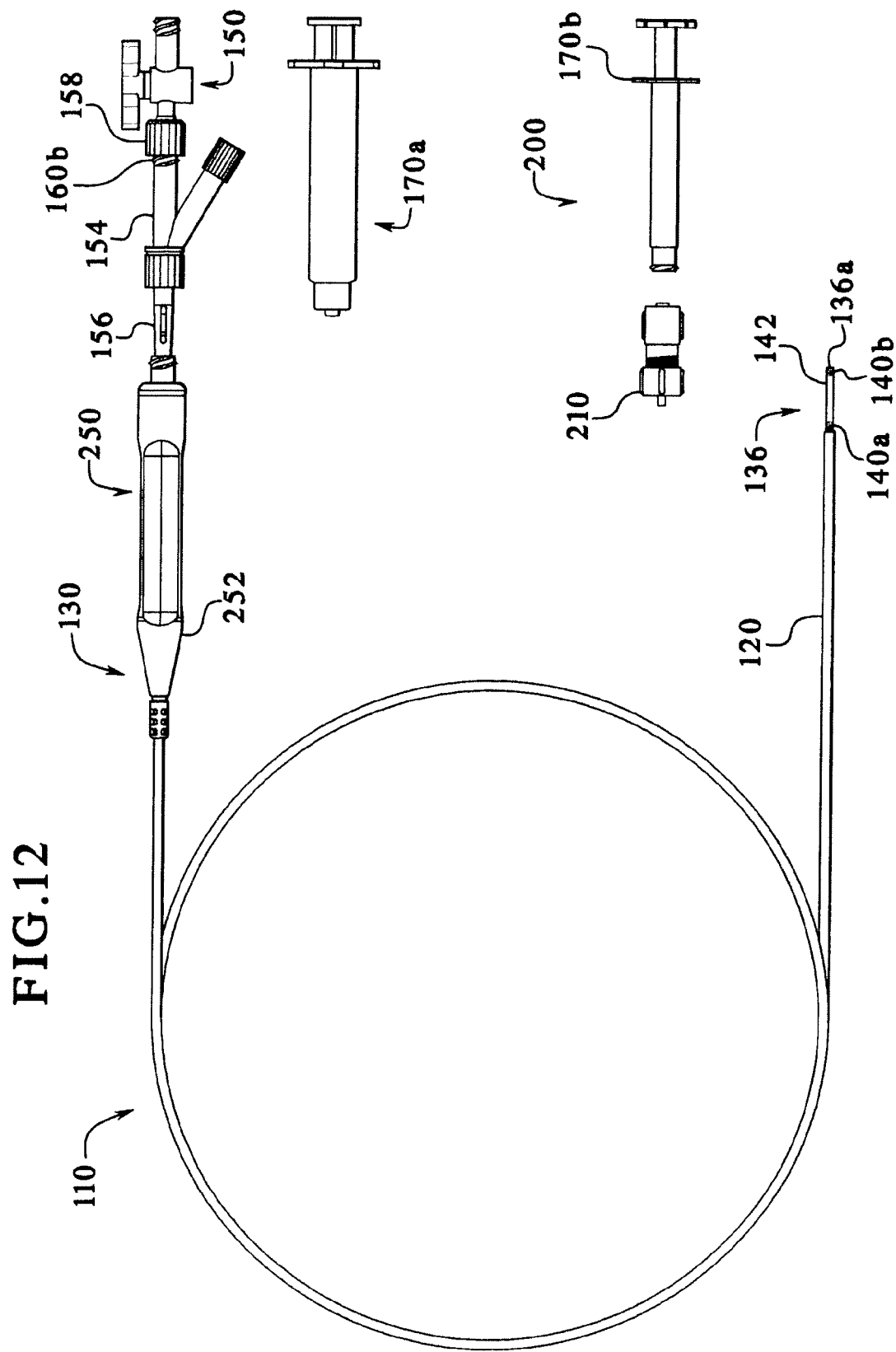
FIG. 12 is an exploded elevation view of another embodiment of a catheter assembly.

Referring now FIGS. 12 to 16, an alternative embodiment for the catheter assembly is illustrate by assembly 110. In FIG. 12, assembly 110 is pulled apart to show an alternative balloon catheter 130. For ease of illustration, outer tube or sheath 120 is not shown in FIGS. 12 and 13 but is shown in FIGS. 14 and 15.

Figure 13:
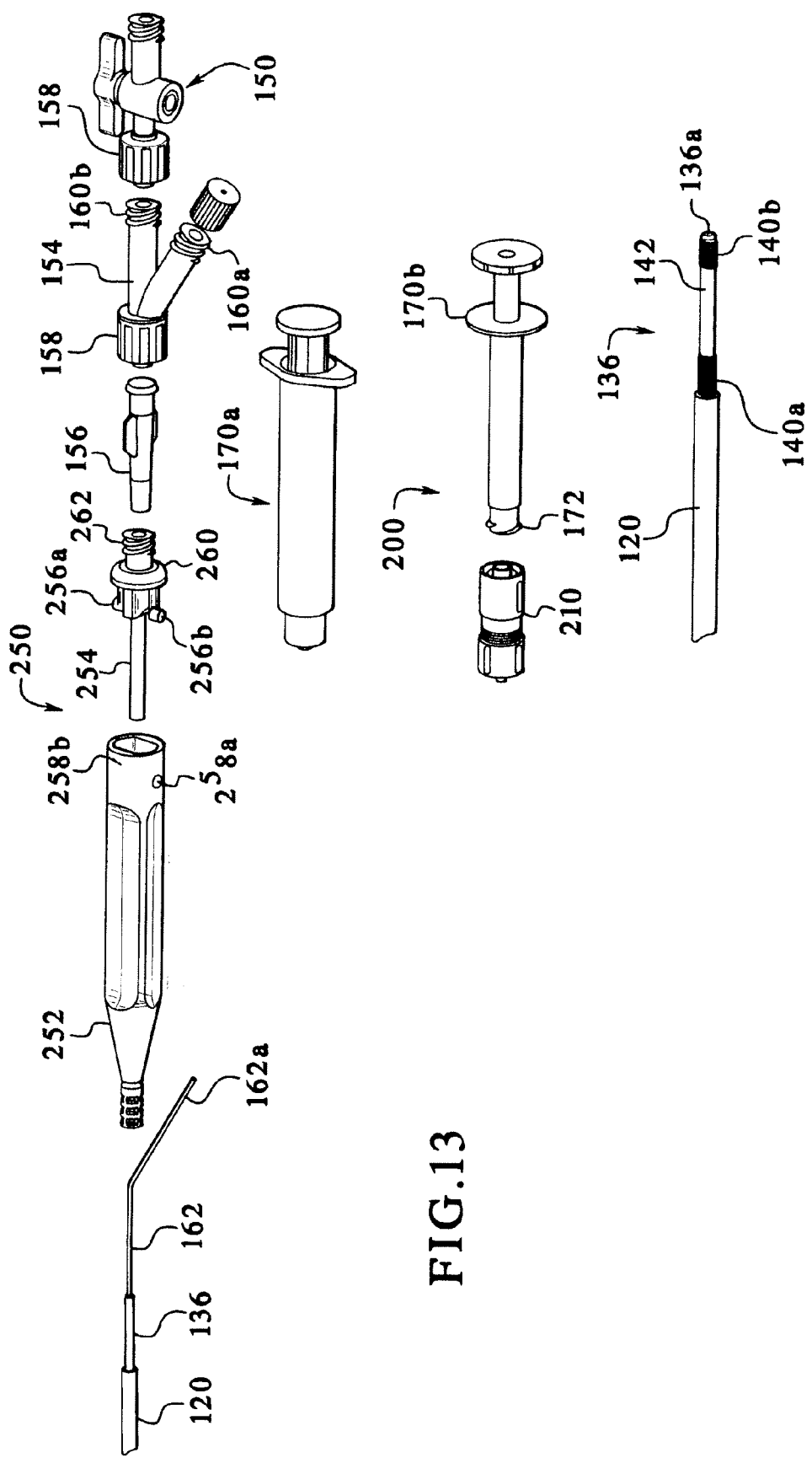
FIG. 13 is an exploded perspective view of the catheter assembly of FIG. 12.

As seen in FIGS. 12 and 13, assembly 110 includes a Y-connector 154, which includes a female luer fitting 160a for receiving a wire cap of a guide wire 162. Guide wire 162 in FIG. 13 includes a bent portion 162a, which a doctor inserts into the branch of Y-connector 154 containing female luer tip 160a and connects eventually to the guide wire cap. Guide wire 162 in an embodiment includes a diameter of about 0.5 mm for 100 mm of length and increases to about 0.75 mm over a second 50 mm of length. In an embodiment, guide wire 162 terminates within about 15 mm from an end 136a of catheter 136. Guide wire 162 can be made via extrusion, centerless grinding, cutting to length and bonding to the wire cap.

Y-connector 154 also includes a female luer fitting 160b for connecting to a male luer fitting 158 of a valve 150. Y-connector 154 it should be appreciated is simplified with respect to the like apparatus shown in connection with FIG. 1A.

Valve 150 performs each of the functions discussed above for valve 50. First, valve 150 connects to a first syringe 170a (e.g., 1 cc to 5 cc) for air pressurization. Second, valve 150 connects to a sub-assembly 200 including an adapter 210 and second syringe 170b. Second syringe 170b (e.g., 1 cc) is preloaded with any of the embodiments discussed above for composition 72. A smaller volume syringe 170b, e.g., 1 cc, is believed to be beneficial because it provides more pressure on composition 72 to extrude the composition from the syringe with less force needing to be applied on the syringe plunger by the doctor. Adapter 210 is shown in detail below in connection with FIG. 16.

Y-connector 154 is connected threadingly to a hub 156. Hub 156 is slidable back and forth with respect to an ergonomic handle 250. FIG. 13 shows that handle 250 includes a handle body 252 and a handle cannula 254 having pegs 256a and 256b that fit into apertures 258a and 258b, respectively, of handle body 252. Hub 156 is tapered such that it bottoms out inside a cap 260 of handle cannula 254 at a point when a distal tip 136a of catheter 136 is extended fully distally out of outer tube or sheath 120, in a position shown in FIG. 12. This position is analogous to that of FIGS. 9 and 10, and the one in which balloon portion 142 of catheter 136 can be inflated. In this manner, hub 156 serves to inform the doctor tactilely when the catheter 136 is in the inflatable position.

As above, balloon portion 142 is sealed on two ends via sutures or windings 140a and 140b. One preferred embodiment for balloon portion 142 is shown and described below in connection with FIGS. 14 and 15.

Cap 260 of handle cannula 254 also includes a female luer tip 262, which accepts a cap (not illustrated) until the doctor is ready to insert the catheter 136, sheath 120 and guide wire 162 through handle 250. Cap 260 of handle cannula 254 is configured with the nose portion of hub 156 to provide an audible and tactile clicking sound and feel when catheter 136 is in the inflatable position.

Sheath 120 can be made of any of the materials listed herein, such as polytetrafluoroethylene ("PTFE"). Handle body 252, handle cap 260, Y-connector 154, valve 150 and the guide wire cap in one embodiment are made of acrylonatrile butadeine styrene ("ABS") and/or polycarbonate. Handle cannula 254 and guide wire 162 in one embodiment are made of stainless steel. Catheter 136 and hub 156 in one embodiment are made of polyether block amides or plasticizer-free thermoplastic elastomers, such as, PEBAX™, Rilsan™ and Wismut™ materials. Balloon portion 142 of catheter 136 in various embodiments is made of at least one of a silicone and latex material. Sutures or windings 140a and 140b in one embodiment are made of PTFE.

Figure 16:
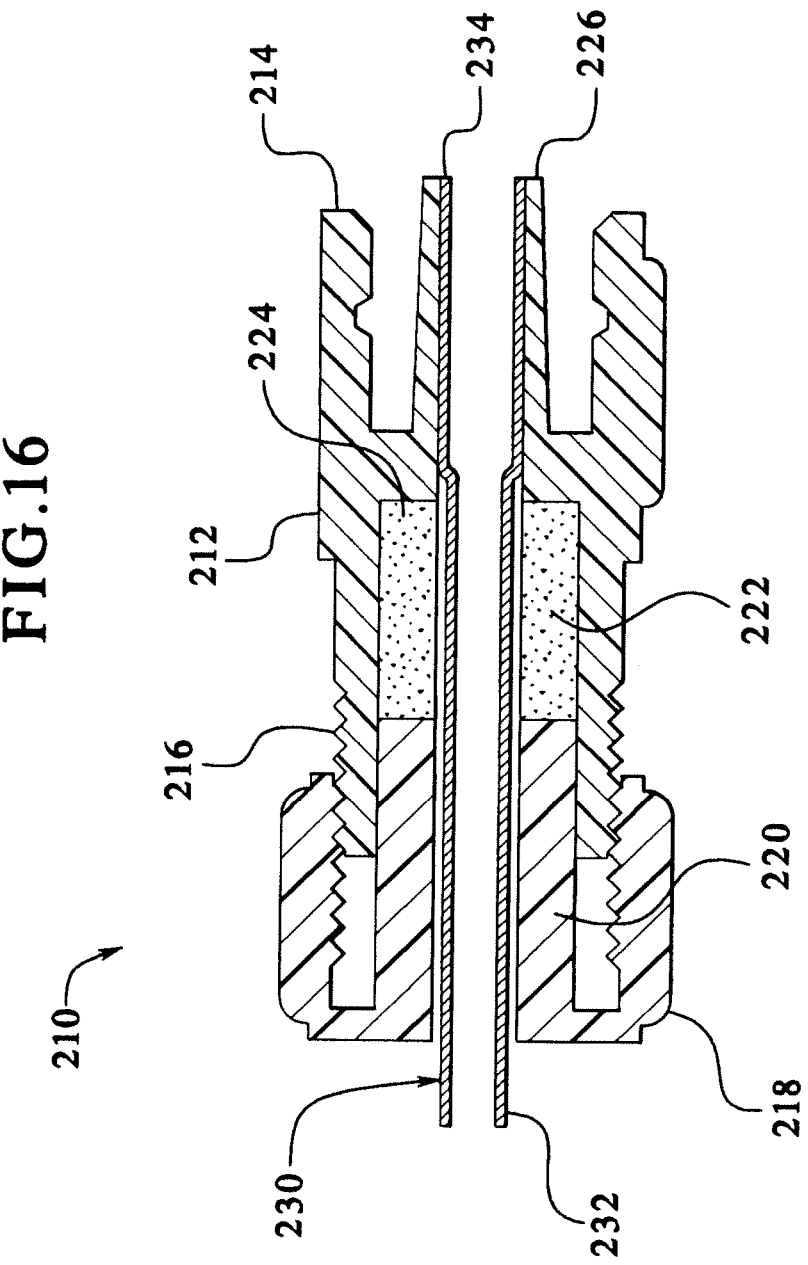
FIG. 16 is a sectioned elevation view of an embodiment of an adapter for fitting a composition carrying syringe to a distal end of the sheath for composition loading.

FIG. 16 illustrates adapter 210 in more detail. Adapter 210 in one embodiment begins with a known Tuohy Borst type of adapter, which can be made for example, from polycarbonate, ABS and/or silicone. Adapter 210 includes a connector 212 having a male luer tip 214 and a male pipe threaded tip 216. Male luer tip 214 connects sealingly to a female luer tip 172 of composition 72 holding syringe 170b. Male pipe threaded tip 216 connects in a tapering threaded manner to a nut 218. Nut 218 includes an inner annular shaped collar 220.

An elastomeric, e.g., silicone, washer 222 is fitted into an annular bore located between male luer tip 214 and a male pipe threaded tip 216 of connector 212. Elastomeric washer 222 has a length such that when nut 218 is loosely threaded onto threaded tip 216, the end of collar 220 just abuts one end of washer 222, while the other end of washer 222 is abutted against a wall 224 of connector 212.

Adapter 210 includes an, e.g., stainless steel, cannula 230 having a smaller diameter end 232 and a larger diameter end 234. Larger diameter end 234 is sized to press or tightly fit into the male luer 226 of male luer tip 214 of connector 212. Larger diameter end 234 can also be adhered to male luer 226 and is in any case fixed within the male luer and thus fixed to adapter 210. As seen in FIG. 16, the length of cannula 230 is sized such that when nut 218 is loosely threaded onto threaded tip 216 of connector 212, smaller diameter end 232 extends past the end of nut 218, e.g., a few millimeters.

After catheter 136 and guide wire 162 have been withdrawn into the sheath (described above in connection with FIG. 3), adapter 210 and composition 72 holding syringe 170b forming subassembly 200 are fitted to the distal end 122 of sheath 120. In an embodiment, distal end 122 of sheath 120 is slid past elastomeric washer 222 located within connector 212. The doctor then tightens nut 218 onto increasingly frictionally engaging threaded end 216 of adapter 210. When this happens, internal collar 220 of adapter 210 translates inwardly with respect to connector 212 and pushes elastomeric washer 222 against wall 224 of the connector. The longitudinal compression of washer 222 causes its inner diameter to shrink down onto the outside of sheath 120, pressing the sheath sealingly against smaller diameter end 232 of metal cannula 230.

The doctor then compresses composition 72 holding syringe 170b to dispense composition 72 into the distal end 122 of sheath 120 to a desired, e.g., black ink, graduation 26 (illustrated above) corresponding to a desired volume of composition 72 (described above in connection with FIG. 4). The connector 212 is removed by loosening the nut 218, which then disengages the washer 22 from the sheath 120 allowing removal of the sheath 120 from connector 212. The loaded sheath 120, catheter 136 and guide wire 162 can then be inserted into the patient (described above in connection with FIG. 5).

As seen in connection with FIGS. 14 and 15, balloon portion 142 of catheter 136 is shaped, configured and sized so that when inflated, it balloons distally past the distal end 136a of catheter 136 and provides a relatively blunt tip 144 having rounded edges. This shields the relatively hard and pointed tip 136a of catheter 136 from contacting the patient's gastrointestinal track and in particular wound site 94, which may be particularly sensitive. It also provides the doctor more flexibility to bend catheter 136 in an attempt to use distal head area 144 of balloon 142 to apply additional and/or more localized pressure to composition 72.

FIG. 14 shows that sutures 140a and 140b, e.g., PTFE yarn, are wrapped around the ends of balloon portion 142, e.g., about 4 mm in from the distal end 136a of catheter 136 and for about 6 mm from the proximal end of balloon portion 142. As illustrated, catheter 136 defines a port 138 to allow compressed gas to expand balloon portion 142. When inflated from a minimum to a maximum profile, the outer radial diameter of balloon portion 142 achieves a minimum size of about 13 mm to a maximum size of about 17 mm. The nominal diameter is about 15 mm, which enables distal end 144 of balloon portion 142 to extend past tip 136a a nominal distance of about 1 mm, which is preferred in one embodiment.

Balloon portion 142 should be configured to inflate centrally about the axis of catheter 136. Balloon portion 142 is made of at least one of a latex and silicone, latex having an extremely high elasticity. Balloon portion 142 can have a 0.1 mm wall thickness, a 1.6 mm outside diameter and a 20 mm length. It can be extruded, cut to length and attached to catheter 136 via sutures 140a and 140b and adhesive.

In an embodiment, the outer diameter of sheath 120 is sized to slide freely inside a 2.8 mm inside diameter of a gastronomical channel scope or introducer 80 (shown above). Sheath diameter can be about 2.5 to 2.55 mm outside diameter by 2.1 mm inside diameter and about 195 cm in length. It is made via extrusion, press-fit over a cannula of handle 250 and cut to length in one embodiment.

The diameter of catheter 136 is sized to slide freely inside of sheath 120. The length of catheter 136 is sized so that it can extend around 10 mm past the end 122 of sheath 120 in one embodiment. It is made of a combination of PEBAX™ plus Rilsan™ and Wismut™ materials with blue colorant in one implementation. Nylon may also be used. Catheter 136 can have dimensions of about 1.65 mm outside diameter and 1.1 mm inside diameter. In an embodiment, the length of catheter 136 is sized in relatively to match its corresponding sheath 120. Catheter 136 can be extruded tubing with a distal end necked down area of 1.4 mm outside diameter by 21 mm length. Hole 138 is drilled in one embodiment. Balloon portion 142, e.g., silicone, is then attached to catheter 136 via sutures 140a and 140b and adhesive. Proximal end of catheter 136 is then cut to length and bonded to hub 156 or other catheter grip discussed herein. Guide wire 162 is then inserted into the catheter.

In an alternative embodiment, a dual lumen catheter is used (not illustrated) providing separate air and wire lumens. The dual lumen catheter reduces the risk of lumen occlusion but decreases a maximum allowable wire size and adds complexity. The dual lumen catheter also allows for a fluid delivery channel through the catheter if it is desired to add fluid to the wound site.

Graduations 26 discussed above in an embodiment are alternating (i) 2 mm wide strips, extending 360 degrees about catheter 136, and marking every 0.5 mL and (ii) 4 mm wide strips, extending 360 degrees about catheter 136, and marking every 0.5 mL. Graduations are printed onto sheath 120 in one embodiment. Graduations 26 may additionally or alternatively appear on composition 72 syringe 170b.

Figure 17:
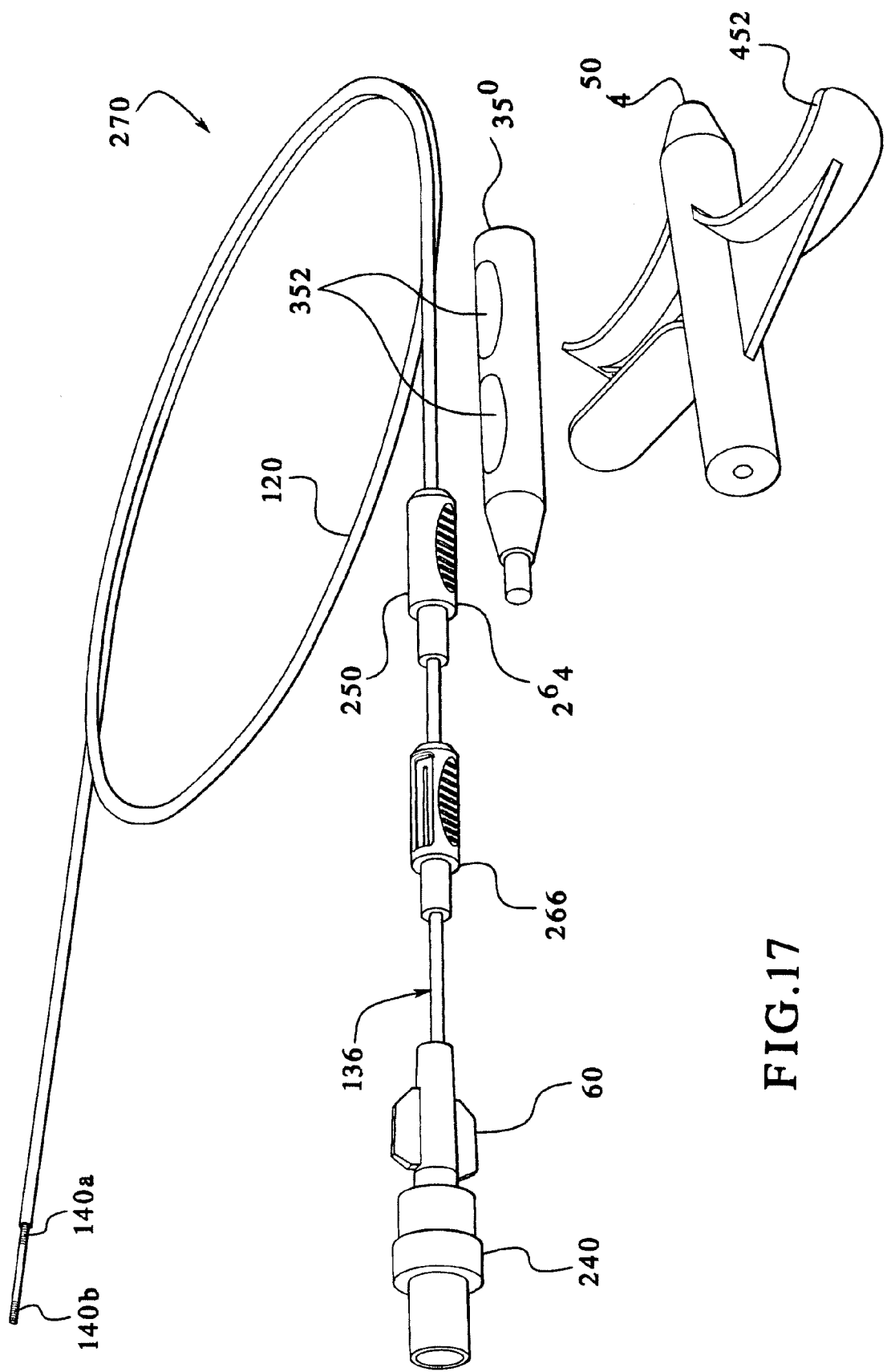
FIG. 17 is a perspective view of a catheter assembly showing an embodiment of a slotted catheter grip and various embodiments for sheath grips.
Figure 18:
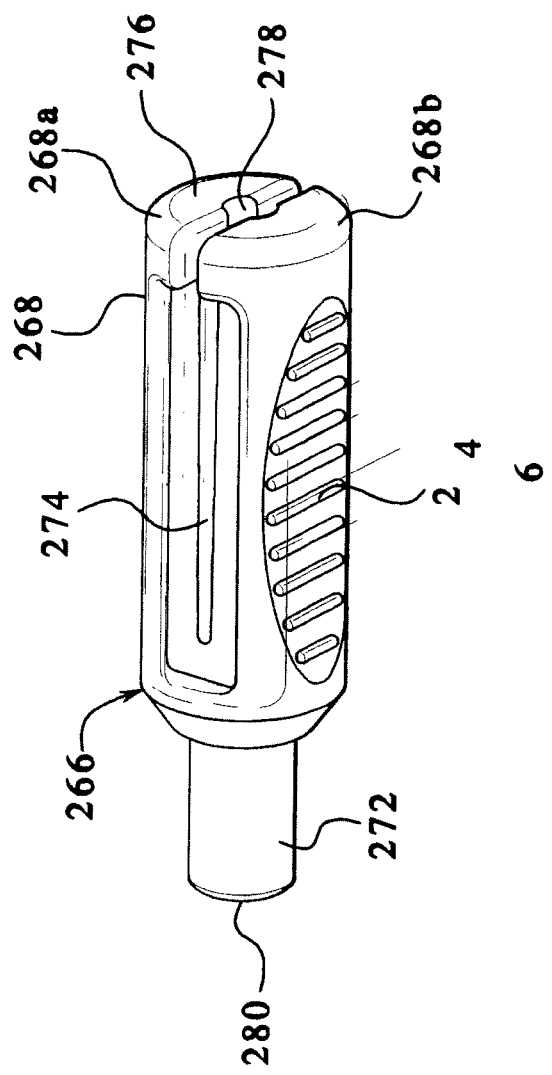
FIG. 18 is an isometric view of an embodiment of the slotted catheter grip of the assembly of FIG. 17.

Referring now to FIGS. 17 and 18, a catheter set 270 having a catheter 136, handle or sheath grip 250 (FIGS. 12 and 13), an, e.g., high density polyurethane ("HDPE") sheath 120, and female luer tip 60 is illustrated. Female luer tip 60 connects to a male luer tip of a luer activated check valve 240 in the illustrated embodiment. Luer activated check valve 240 replaces valve or stopcock 150 shown above. Handle or sheath grip 250 is bonded to sheath 120 and includes ergonomically ribbed grasping portions 264.

FIG. 17 illustrates a first alternative handle or sheath grip 350, which is also bonded to sheath 120, is elongated relative to sheath grip 250, and includes or defines grasping wells 352. A second alternative handle or sheath grip 450 is bonded to sheath 120, is elongated relative to sheath grip 250 and includes or defines gusseted flanges 452. Grasping portions 264, grasping wells 352 and gusseted flanges 452 each aid the doctor in holding sheath 120 steady relative to the motion of catheter 136 during application of composition 72.

Hub 156 of assembly 110 in FIG. 17 is replaced by a slotted gripper 266 shown in more detail in FIG. 18. Slotted gripper 266 also has ribbed grasping portions 264 and is made of any suitable material listed herein. Slotted gripper 266 includes a larger diameter slotted portion 268 and a smaller diameter stopper portion 272. Larger diameter slotted portion 268 defines a slot 274, which extends through a distal end 276 of larger diameter slotted portion 268, causing two halves 268a and 268b of slotted portion 268 to bow slightly outwardly at end 276. Halves 268a and 268b together define a cylindrical aperture 278, having a diameter sized so that when the doctor compresses halves 268a and 268b, they come together to grip catheter 136. At that point the doctor can move gripper 266 to move catheter 136 relative to handle 250 and sheath 120.

When the doctor releases halves 268a and 268b, the halves spring apart so that larger diameter slotted portion 268 and a smaller diameter stopper portion 272 can slide freely relative to catheter 136. In an embodiment, catheter 136 is provided with tactile feedback apparatus (not illustrated), which contacts the proximal end 280 of smaller diameter stopper portion 272 when catheter 236 is in the proper position for inflating balloon portion 142 or would be in the inflating position assuming gripper 266 is pushed all the way to sheath grip 250, 350 or 450. Alternatively, the proximal end 280 of smaller diameter stopper portion 272 is backed up to female luer tip 60, catheter 136 is grasped and pushed until distal end 276 abuts handle 250, 350 or 450 to push catheter 236 into the proper position for inflating balloon portion 142.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A medical catheter system comprising:
    a source of a composition that may be applied to an internal wound site of a mammalian body; and
    a catheter assembly including,
        an outer tube having a proximal end and a distal end,
        a balloon catheter located within the outer tube, the balloon catheter moveable within the outer tube so as to create an open space within the outer tube at the distal end thereof, wherein an amount of the composition supplied by the source is sufficient to fill the open space created between the balloon catheter and the distal end of the outer tube; and
        a connector located at the distal end of the outer tube, the connector configured to receive the source to supply the sufficient amount of composition into the open space created between the balloon catheter and the distal end of the outer tube.

2. The medical catheter system of claim 1, wherein the source of the composition includes a syringe filled with the composition.

3. The medical catheter system of claim 1, wherein a proximal end of the balloon catheter includes at least one of: (i) a valve and (ii) at least one connector configured to receive a guide wire.

4. The medical catheter system of claim 1, wherein the composition is of at least one type selected from the group consisting of: (i) a biocompatible polymeric composition; (ii) a molecular, cross-linked hydrogel; (iii) a dry powder; (iv) a partially hydrated gel; and (v) a fully hydrated gel.

5. The medical catheter system of claim 1, wherein the composition is configured to be applied additionally: (i) for supplementing tissues; (ii) for filling soft and hard tissue regions, divots, tracts, body cavities, present in muscle, skin, epithelial tissue, connective or supporting tissue, nerve tissue, ophthalmic and other sense organ tissue, vascular and cardiac tissue, gastrointestinal organs and tissue, pleura and other pulmonary tissue, kidney, endocrine glands, male and female reproductive organs, adipose tissue, liver, pancreas, lymph, cartilage, bone, oral tissue, and mucosal tissue; (iii) for filling soft implantable devices, breast implants; and (iv) with drugs and active agents to release the drugs or agents at a target site over time.

6. The medical catheter system of claim 1, which includes at least one of: (i) a tip protector fitted to the distal end of the outer tube; (ii) a bag sealable to enclose the source and catheter assembly prior to use; and (iii) an introducer.

7. The medical catheter system of claim 1, which includes a slotted gripper fitted slideably over the catheter assembly, the slotted gripper releasably compressible to grasp and move the catheter assembly.

8. A medical catheter assembly comprising:
    an outer tube having a proximal end and a distal end; and
    a balloon catheter located within the outer tube, the balloon catheter moveable within the outer tube so as to create an open space within the outer tube at the distal end thereof, the open space sized to hold a composition configured to be applied to an internal wound site of a mammalian body in an amount sufficient to cover the wound site; and
    an applicator configured to sealingly engage a distal end of the outer tube to deliver the composition to the open space created between the balloon catheter and the distal end of the outer tube.

9. The medical catheter assembly of claim 8, wherein the distal end of the outer tube includes a connector configured to mate with a mating connector of the applicator.

10. The medical catheter system of claim 8, wherein the applicator includes an adapter configured to fit over a distal end of the outer tube, such that the outer tube is sealable between a washer and a cannula of the adapter for transfer of the composition to the open space.

11. The medical catheter system of claim 10, wherein the adapter is further configured to mate with a syringe initially holding the composition.

12. The medical catheter assembly of claim 8, wherein the distal end of the outer tube includes graduations indicating volumetric units applicable to the open space.

13. The medical catheter assembly of claim 8, wherein the balloon catheter includes a pre-incorporated guide wire.

14. A medical catheter assembly comprising:
    a sheath having a proximal end and a distal end;
    a connector disposed at the distal end of the sheath;
    a catheter forming an exterior surface located within the sheath, the catheter moveable within the sheath so as to create an open space within the sheath;
    a substantially rigid guide member removably inserted within the catheter having a proximal end and a distal end; and
    a balloon forming two ends, the ends secured to the exterior surface of the catheter, the catheter forming a port between the two ends such that when gas is applied through the catheter to the balloon, the gas flows through the port into the balloon and the balloon expands and extends longitudinally past a distal end of the catheter,
    wherein the open space extends from the proximal end of the sheath to the distal end of the sheath and the connector is configured to facilitate a filling of a composition into the open space before insertion of the medical catheter assembly into a mammalian body.

15. The medical catheter assembly of claim 14, wherein the open space is sized to hold the composition configured to be applied from a source to an internal wound site of the mammalian body.

16. The medical catheter assembly of claim 14, wherein the balloon is secured to the catheter via at least one of: adhesive and suture windings.

17. The medical catheter assembly of claim 14, wherein the balloon is made of at least one of latex and silicone.

18. The medical catheter assembly of claim 14, wherein a distal end of the balloon when expanded is at least one of: relatively blunt, rounded and about 1 mm longitudinally past the distal end of the catheter.

19. A medical catheter system comprising:
    a composition that may be applied to an internal wound site of a mammalian body; and
    a catheter assembly including:
        an outer tube having a proximal end and a distal end, and
        a balloon catheter including a balloon located within the outer tube, the balloon catheter configured to be moveable within the outer tube so as to extend the balloon out of the distal end of the outer tube and to be retracted within the outer tube to form an open space extending from a distal end of the catheter to the distal end of the outer tube, the composition residing within the open space upon insertion of the outer tube into the mammalian body.

20. The medical catheter system of claim 1, wherein the connector comprises a female luer connector.

21. The medical catheter assembly of claim 14, wherein the catheter forms a distal end and both ends of the balloon are secured to the exterior surface of the cannula proximal the distal end of the catheter.

22. The medical catheter assembly of claim 15, where a portion of the balloon extending between the ends of the balloon extends distal the distal end of the catheter upon expansion of the balloon with the gas.

23. The medical catheter assembly of claim 8, wherein the applicator is configured to sealingly engage the distal end of the catheter.

24. The medical catheter assembly of claim 8, wherein the applicator is attached to the outer tube.

\* \* \* \* \*